(12) United States Patent
Li et al.

(10) Patent No.: US 9,612,234 B2
(45) Date of Patent: *Apr. 4, 2017

(54) DATA ANALYSIS OF IMPEDANCE-BASED CARDIOMYOCYTE-BEATING SIGNALS AS DETECTED ON REAL-TIME CELL ANALYSIS (RTCA) CARDIO INSTRUMENTS

(75) Inventors: Nan Li, San Diego, CA (US); Xiaobo Wang, San Diego, CA (US); Yama A. Abassi, San Diego, CA (US); Biao Xi, San Diego, CA (US); Wen Fu Zhang, San Diego, CA (US); Xiao Xu, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 669 days.

This patent is subject to a terminal disclaimer.

(21) Appl. No.: 13/109,809

(22) Filed: May 17, 2011

(65) Prior Publication Data

US 2011/0300569 A1    Dec. 8, 2011

Related U.S. Application Data

(63) Continuation-in-part of application No. 12/435,569, filed on May 5, 2009.

(Continued)

(51) Int. Cl.
*C40B 30/06*    (2006.01)
*G01N 7/00*    (2006.01)
(Continued)

(52) U.S. Cl.
CPC ..... *G01N 33/5061* (2013.01); *G01N 33/4836* (2013.01); *G01N 33/5008* (2013.01); *G01N 33/5014* (2013.01); *G01N 2800/52* (2013.01)

(58) Field of Classification Search
CPC .......... G01N 33/4836; G01N 2800/52; G01N 33/5008; G01N 33/5014; G01N 33/5061
See application file for complete search history.

(56) References Cited

U.S. PATENT DOCUMENTS 2,656,508 A    10/1953  Coulter
3,259,842 A    7/1966  Coulter et al.
(Continued)

FOREIGN PATENT DOCUMENTS

EP    1138758    10/2001
EP    1195432    4/2002
(Continued)

OTHER PUBLICATIONS

Banach et al., Development of electrical activity in cardiac myocyte aggregates derived from mouse embryonic stem cells, Am. J. Physiol. Heart Circ. Physiol., 2003, vol. 284, pp. H2114-H2123.*
(Continued)

*Primary Examiner* — Reza Ghafoorian
(74) *Attorney, Agent, or Firm* — Wagenknecht IP Law Group PC

(57) ABSTRACT

A method of determining one or more beating parameters for use in cardiomyocyte beating analysis including: providing a cell analysis device including wells, each well including a sensor capable of monitoring beating of cardiomyoctes in millisecond time resolution; adding cardiomyocytes to the wells; monitoring the beating of the cardiomyocytes in millisecond time resolution to obtain a plurality of beating measurements; and calculating one or more beating parameters from the plurality of beating measurements.

18 Claims, 28 Drawing Sheets

Related U.S. Application Data

(60) Provisional application No. 61/191,684, filed on Sep. 11, 2008, provisional application No. 61/126,533, filed on May 5, 2008, provisional application No. 61/345,867, filed on May 18, 2010.

(51) Int. Cl.
    *C12Q 1/00* (2006.01)
    *G01N 33/50* (2006.01)
    *G01N 33/483* (2006.01)

(56) References Cited

U.S. PATENT DOCUMENTS

| | | |
|---|---|---|
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao et al. |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Muller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1* | 2/2005 | Cantor ............... 435/288.3 |
| 6,998,249 B1 | 2/2006 | McKim et al. |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadler et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Abassi et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 2002/0090649 A1 | 7/2002 | Chan et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2004/0152067 A1* | 8/2004 | Wang ............... G01N 33/5005 435/4 |
| 2005/0014130 A1 | 1/2005 | Liu et al. |
| 2005/0153425 A1* | 7/2005 | Xu et al. ............. 435/287.1 |
| 2005/0182447 A1* | 8/2005 | Schecter ............... 607/2 |
| 2006/0050596 A1* | 3/2006 | Abassi ............... C12Q 1/002 365/230.06 |
| 2006/0057771 A1 | 3/2006 | Kovacs et al. |
| 2006/0161073 A1 | 7/2006 | Singer et al. |
| 2006/0216203 A1 | 9/2006 | Fuller et al. |
| 2007/0042347 A1 | 2/2007 | Rosen et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu et al. |
| 2009/0142790 A1 | 6/2009 | Fang et al. |
| 2010/0029506 A1 | 2/2010 | Wang et al. |
| 2011/0039294 A1 | 2/2011 | Wang et al. |
| 2011/0300569 A1 | 12/2011 | Li et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0185206 A1 | 7/2015 | Abassi et al. |

FOREIGN PATENT DOCUMENTS

| | | |
|---|---|---|
| EP | 1 040 345 B1 | 3/2006 |
| EP | 2291645 | 9/2015 |
| WO | 96/01836 | 1/1996 |
| WO | 99/66329 | 12/1999 |
| WO | 00/37628 | 6/2000 |
| WO | 00/70343 | 11/2000 |
| WO | 00/71669 | 11/2000 |
| WO | 01/25769 | 4/2001 |
| WO | 01/38873 | 5/2001 |
| WO | 01/79529 | 10/2001 |
| WO | 02/004943 | 1/2002 |
| WO | 02/42766 | 5/2002 |
| WO | 03/016887 | 2/2003 |
| WO | 2004/010103 | 1/2004 |
| WO | 2005/005979 | 1/2005 |
| WO | 2005/047482 | 5/2005 |

(56) References Cited

FOREIGN PATENT DOCUMENTS

| WO | 2005/077104 | 8/2005 |
|---|---|---|
| WO | 2006/017762 | 2/2006 |
| WO | 2009/137440 | 11/2009 |
| WO | 2010/129725 | 11/2010 |
| WO | 2011/146531 | 11/2011 |
| WO | 2012/043820 | 4/2012 |
| WO | 2014/085727 | 6/2014 |

OTHER PUBLICATIONS

Hescheler et al., Determination of electrical properties of ES cell-derived cardiomyocytes using MEAs, 2004, Journal of Electrocardiology, vol. 37, pp. 1 10-116.*
Horvath et al., Monitoring of living cell attachment and spreading using reverse symmetry waveguide sensing, Applied Physics Letters 86, 071101 (2005).*
Qiu et al., Real-Time Monitoring Primary Cardiomyocyte Adhesion Based on Electrochemical Impedance Spectroscopy and Electrical Cell-Substrate Impedance Sensing. Anal. Chem. 2008, 80, 990-996.*
Bauman et al, Microelectronic sensor system for microphysical application on living cells, Sensors and Actuators, 1999:77-89.
Berens et al., The role of extracelluar matrix in human astrocytoma migration and proliferation studied in a microliter scale assay, Clin. Exp. Metastasis, 1994; 12(6):405-415.
Bieberich et al., Neuronal differentiation and synapse formation of PC12 and embryonic stem cells on interdigitated microelectrode arrays: Contact structures for neuron-to-electrode signal transmission (NEST), Biosensors and Bioelectronics 2004; 19:923-931.
Burnett et al., Fluorescent imaginng of electrically stimulated cells, Journal of Biomolecular Screening 2003; 8 (6):660-667.
Cady et al, Electrical Impedance Measurements: Rapid Method for Detecting and Monitoring Microorganisms, J. Clin. Mirobiol., 1978; 7(3):265-272.
Ehret et al., Monitoring of cellular behaviour by impedance measurements on interdigitated electrode structures, Biosensors and Bioelectronics 1997; 12(1):29-41.
Ehret et al., On-line control of cellular adhesion with impedance measurements using interdigitated electrode structures, Med. Biol. Eng. Comput., 1998; 36:365-370.
Giaever et al., Micromotion of mammalian cells measured electrically, Proc. Natl. Acad. Sci. USA, 1991; 8 (Sept.):7896-7900.
Giaever et al., Monitoring fibroblast behavior in tissue culture with an applied electric field, Proc. Natl. Acad. Sci. USA; 1984; 81(June):3761-3764.
Henning et al., Approach to a mutliparametric sensor-chip-based tumor chemosensitivity assay, Anti-Cancer Drugs 2001; 12:21-32.
Hidalgo et al., Characterization of the human colon carcinoma cell line (Caco-2) as a model system for intestinal epithelial Permeability, 1989; 96:736-749.
Hug, Thomas, Biophysical methods for monitoring cell-substrate interactions in drug discovery, Assay and Drug Development Technologies, 2003; 1(3):479-488.
Kleinman et al., Basement membrane complexes with biological activity, Biochemistry 1986; 25(2):312-318.
Kowolenko et al., Measurement of macrophage adherence and spreading with weak electric fields, Journal of Immunological Methods, 1990; 127:71-77.
Lo et al., Monitoring motion of confluent cells in tissue culture, Experimental Cell Research 1983; 204:102-109.
Luong et al., Monitoring motility, spreading and mortality of adherent insect cells using an impedance sensor, Anal. Chem 2001; 73(8):1844-1848.
Neher, Erwin, Molecular biology meets microelectronics, Nature Biotechnology, 2001; 19:114.
Ong et al., Remote query resonant-circuit sensors for monitoring of bacterial growth: Application to food quality control, Sensors 2002; 2:219-232.
Pancrazio et al., Portable cell-based biosensor system for toxin detection, Sensors and Actuators 1998; 53:179-185.
Slaughter et al., Artificial neural network for temporal impedance recognition of neurotoxins, 2006 International Joint Conference on Neural Networks 2006; Jul. 16-21: 2001-2008.
Stenger et al., Detection of physiologically active compounds using cell-based biosensors, Trends in Biotechnology, 2001; 19(8):304-309.
Wang et al., A theoretical method of electrical field analysis for dielectrophoretic electrode arrays using Green's theorem, J. Phys. D: Appl. Phys 1996; 29:1649-1660.
Wegener et al., Electric cell-substrate impedance sensing (ECIS) as noninvasive means to monitor the kinetics of cell spreading to artificial surfaces, Experimental Cell Research 2000; 259:158-166.
Wolf et al., Monitoring of cellular signalling and metabolism with modular sensor-technique: The PhysioControl-Microsystem (PCM), Biosensors and Bioelectronics 1998; 13:501-509.
Xiao et al., Assessment of cytotoxicity using electric cell-substrate impedance sensing: Concentration and time response function approach, Anal. Chem 2002, 74:5748-5753.
Xiao et al., An in-depth analysis of electric cell-substrate impedance sensing to study the attachment and spreading of mammalian cells, Anal. Chem 2002; 74(6):1333-1339.
Xiao et al., On-line monitoring of cell growth and cytotoxicity using electric cell-substrate impedance sensing (ECIS), Biotechnol. Prog. 2003; 19:1000-1005.
Berdondini et al. "High-density electrode array for imaging in vitro electrophysiological activity." Biosensors and Bioelectronics, 2005, 21:167-174.
Chang et al. "Impedimetric monitoring of cell attachment on interdigitated microelectrodes." Sensors and Actuators, 2005, B 105:159-163.
Yang et al. "A novel microfluidic impedance assay for monitoring endothelin-induced cardiomyocyte hypertrophy." Biosensors and Bioelectronics, 2007, 22:1688-1693.
PCT/US2009/033801 International Search Report and Written Opinion mailed Jul. 9, 2010.
PCT/US2009/042787 International Search Report and Written Opinion mailed Jun. 24, 2009.
PCT/US2011/036877 International Search Report mailed Sep. 2, 2011.
PCT/US2013/072439 International Search Report mailed Feb. 19, 2014.
PCT/US2005/034561 International Preliminary Report on Patentability mailed Mar. 27, 2007.
PCT/US2005/034561 International Search Report mailed Sep. 27, 2006.
PCT/US2005/027943 International Preliminary Report on Patentability mailed Apr. 11, 2007.
PCT/US2005/027943 International Search Report and Written Opinion mailed Mar. 21, 2007.
PCT/US2004/037696 International Search Report mailed May 16, 2005.
PCT/US2005/04481 International Search Report mailed Sep. 12, 2005.
EP05722991 Extended European Search Report mailed Apr. 3, 2009.
EP11193882 Extended European Search Report mailed Apr. 5, 2012.
EP13171137 Extended European Search Report mailed Aug. 16, 2013.
EP05786773 Extended European Search Report mailed Mar. 21, 2013.
EP05852157 Extended European Search Report mailed Sep. 13, 2011.
EP058122680 Extended European Search Report mailed Sep. 7, 2011.
EP03748948 Extended European Search Report mailed Mar. 12, 2007.
CA2556219 Office Action mailed Aug. 9, 2010.
CA2575573 Office Action mailed Apr. 4, 2012.
EP09743420 European Search Report mailed Nov. 26, 2013.

(56) References Cited

OTHER PUBLICATIONS

Kloss et al. "Microcavity array (MCA)-based biosensor chip for functional drug screening of 3D tissue models" Biosensors and Bioelectronics, 2008, 23:1473-1480.
Oka et al. "A new planar multielectrode array for extracellular recording: application to hippocampal acute slice." Journal of Neuroscience Methods, 1999, 93:61-67, Elsevier Science, B.V.
Qiu et al. "Real-Time Monitoring Primary Cardiomyocyte Adhesion Based on Electrochemical Impedance Spectroscopy and Electrical Cell-Substrate Impedance Sensing" Anal. Chem., 2008, 80:990-996.
Yu et al. "Real-Time Monitoring of Morphological Changes in Living Cells by Electronic Cell Sensor Arrays: An Approach to Study G Protein-Coupled Receptors" Anal. Chem., 2006, 78:35-43.
Xing et al. "Dynamic Monitoring of Cytotoxicity on Microelectronic Sensors" Chem. Res. Toxicol., 2005, 18 (2):154-161.
Blagbrough et al. "Polyamines and novel polyamine conjugates interact with DNA in ways that can be exploited in non-viral gene therapy." Biochemical Society Transactions, 2003, 31, Part 2, pp. 397-406.
Bonetta, Laura. "The inside scoop-evaluating gene delivery methods." Nature Methods, Nov. 2, 2005, (11):875-883.
Hapala, Ivan. "Breaking the Barrier: Methods for Reversible Permeabilization of Cellular Membranes." Critical Reviews in Biotechnology, 1997, 17(2):105-122.
Loffert et al. "Multiplex PCR with QIAGEN: Taq DNA Plymerase and PCR Buffer." QIAGENews, 1994, 4:15-18.
Luan and Li. "Clustering of time-course gene expression data using a mixed-effects model with B-splines." Bioinformatics, 2003, 19(4):474-482.
Nicoazzi et al. "Cationic Lipids for Transfection." Current Medicinal Chemistry, 2003, 10:1263-1277.
Rabow et al. "Mining the National Cancer Institute's Tumor-Screening Database: Identification of Compounds with Similar Cellular Activities." J. Med. Chem., 2002, 45:818-840.
Steinem et al. "Impedance and shear wave resonance analysis of ligand-receptor interactions at functionalized surfaces and of cell monolayers." Biosensors & Bioelectronics, 1997, 12(8):787-808.
Patolsky et al., Detection of single-base DNA mutations by enzyme-amplified electronic transduction. Nature Biotechnology 19:253-257 (2001).
Pethig et al., Positive and negative dielectrophoretic collection of colloidal particles using interdigitated castellated microelectrodes. Appl. Phys. 24:881-888 (1992).
Richards et al., A Modified Microchamber Method for Chemotaxis and Chemokinesis. Immunological Communications 13(1):49-62.
Rishpon et al., An Amperometric Enzyme-channeling Immunosensor. Biosensors & Bioelectronicsd, 12(3):195-204 (1997).
Simpson et al. "Whole-cell biocomputing." Trends in Biotechnology, 2001, 19(9):317-323.
Sohn et al. "Capacitance cytometry: Measuring biological cells one by one." Proc. Nat. Acad. Sci., 2000, 97 (20):10687-10690.
Svetlicic et al. "Charge Displacement by adhesion and spreading of a cell." Bioelectrochemistry, 2000, 53:79-86.
Tiruppathi et al. "Electrical method for detection of endothelial cell shape change in time: assessment of endothelial barrier function." Proc Natl Acad Sci USA, 1992, 89:7919-7923.
Wang et al. "Selective Dielectrophoretic confinement of bioparticles in potential energy wells." Appl. Phys., 1993, 26:1278-1285.
Wang et al. "Cell Separation by Dielectrophoretic Field-flow-fractionation." Anal. Chem., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." In Biochip Technology (eds), pp. 135-159, Harwood Academic Publishers, PA, USA.
Aravanis et al. "A genetically engineered cell-based biosensor for functional classification of agents." Biosensors & Bioelectronics, 2001, 16:571-577.
Baumann et al. "Microelectronic sensor system for microphysiological application on living cells." Sensors & Accuators, 1999, B55:77-89.
Becker et al. "Separation of human breast cancer cells from blood by differential dielectric affinity." Cell Biology, 1995, 92:960-964.
Berens et al. "The role of extracellular matrix in human astrocytoma migration and proliferation studied in a microliter scale assay." Clin. Exp. Metastasis, 1994, 12:405-415.
Bergveld, P. "A critical evaluation of direct electrical protein detection methods." Biosensors & Bioelectronics. 6:55-72 (1991).
Burns et al. "Neutrophil Transendothelial Migration Is Independent of Tight Junctions and Occurs Preferentially at Tricellular Corners." Journal of Immunology, 1997, 2893-2903.
Ciambrone et al. "Cellular Dielectric Spectroscopy: A Powerful New Approach to Label-Free Cellular Analysis." J. Biomo. Screening, 2004, 9(6):467-480.
Duan et al. "Separation-Free Sandwich Enzyme Immunoassays Using Microporous Gold Electrodes and Self-Assembled Monolayer/lmmobilized Capture Antibodies." Anal. Chem., 1994, 66:1369-1377.
Gutmann et al. "Evidence for Different ABC-Transporters in Caco-2 Cells Modulating Drug Uptake." Pharmaceutical Research, 1999, 16(3):402-407.
Hug, Thomas S. "Biophysical Methods for Monitoring Cell-Substrate Interactions in Drug Discovery." Assay and Drug Dev. Tech., 2003, 1(3):479-488.
Lin and Huang. "Electroporation microchips for in vitro gene transfection." J. Micromech. Microeng., 2001, 11:542-547.
Lin et al. "Simulation and experimental demonstration of the electric field assisted electroporation microchip for in vitro gene delivery enhancement" Min. for Chem., Bio., & Bioeng., 2004, 4:104-108.
Lo et al. "Impedance Analysis of MDCK cells measured by electric cell-substrate impedance sensing." Biophysical Journal, 1995, 69:2800-2807.
Mitra et al. "Electric measurements can be used to monitor the attachment and spreading of cells in tissue culture." Biotechniques, 1991, 11(4):504-510.
Miyata et al. "New Wound-Healing Model Using Cultured Corneal Endothelial Cells." Jpn. J. Opthalmol., 1990, 34:257-266.
Mohr et al. "Performance of a thin film microelectrode array for monitoring electrogenic cells in vitro." Sensors and Actuators, 1996, B34:265-269.
Nerurkar et al. "The Use of Surfactants to Enhance the Permeability of Peptides Through Caco-2 Cells by Inhibition of an Apically Polarized Efflux System" Pharmaceutical Research, 1996, 13(4):528-534.
"Molecular Viewer" New Products page. Science, 298:2409 (2002).
"Cell Migration Studies with TECAN Systems." TECAN., Sep. 1999, [retrieved from the internet] http://www.tecan.com/migration_introl.pdf, 10 pgs.
"Detect Cell Migration and Invasion in a Homogeneous Fluorescent Assay System." BD Biosciences, [retrieved from the internet] http://www.bdbiosciences.com/discovery_labware/Products/inserts/BD_Falcon_HTS_fluoroblok_inserts/individual_fluoroblok_inserts/index.html, 2004.
"Neuro Probe AA96, AB96, AC96 Chemotaxis Chambers." Neuro Probe, [retrieved from the internet] http://www.neuroprobe.com/protocol/pt_96a.html, 5 pgs.
"Automated Cell Monitoring Instrument." Applied BioPhysics, 2002, [retrieved from the internet] http://www.biophysics.com/pages/front/html, 1 page.
Yamauchi et al. "Spatially and temporally controlled gene transfer by electroporation into adherent cells on plasmid DNA-loaded electrodes." Nuc. Acids Res., 2004, 32(22):1-8.
Yang et al. "Celli Separation on Microfabricated Electrodes Using dielectrophoretic/Gravitational field-flow Fractionation." Anal. Chem., 1999, 71:911-918.

(56) References Cited

OTHER PUBLICATIONS

Connolly et al. "An extracellular microelectrode array for monitoring electrogenic cells in culture." Biosensors & Bioelectronics, 1990, 5:223-234.

Falk et al. "A 48-well Micro Chemotaxis Assembly for Rapid and Accurate Measurement of Leukocyte Migration." J. Immunol. Meth., 1980, 33:239-247.

Fuhr et al. "Positioning and Manipulation of Cells and Microparticles Using Miniaturized Electric Field Traps and Travelling Waves." Sensors and Materials 7(2):131-146 (1995).

Hadjout et al., Automated Real-Time Measurement of Chemotactic Cell Motility Biotechniques 31:1130-1138 (2001).

Huang et al., Dielectrophoretic Cell Separation and Gene Expression Profiling on Microelectronic Chip Arrays. Anal. Chem. 74:3362-3371 (2002).

Keese et al., Real-time impedance assay to follow the invasive activities of metastatic cells in culture. Biotechniques, 2002, 33:842-850.

Larsen et al. "Somatic Cell Counting with Silicon Apertures." Micro Total Analysis Systems, 2000, 103-106.

Lo et al. "pH Changes in pulsed CO2 incubators cause periodic changes in cell morphology." Experimental Cell Research, 213:391-397 (1994).

Wegener et al. "Electric cell-substrate impedance sensing system (ECIS) as a noninvasive means to monitor the kinetics of cell spreading to artificial surfaces." Eur. J. Physiol., 1999, 437:925-934.

\* cited by examiner

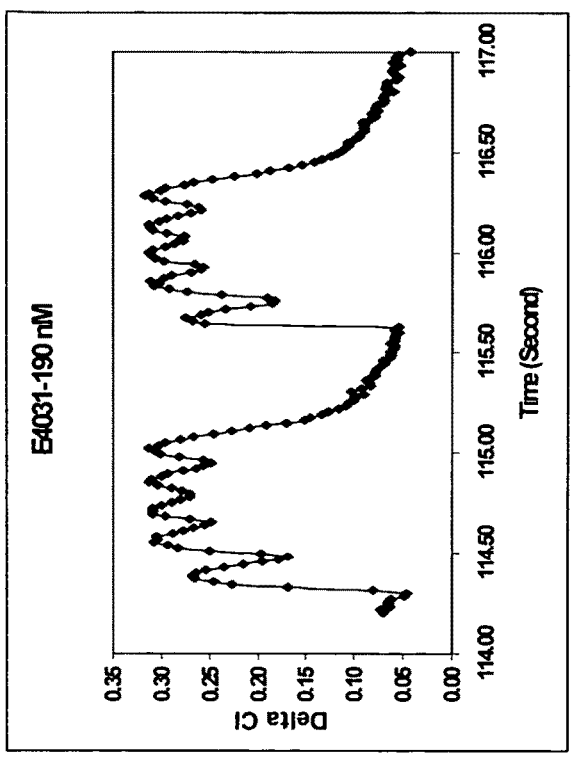
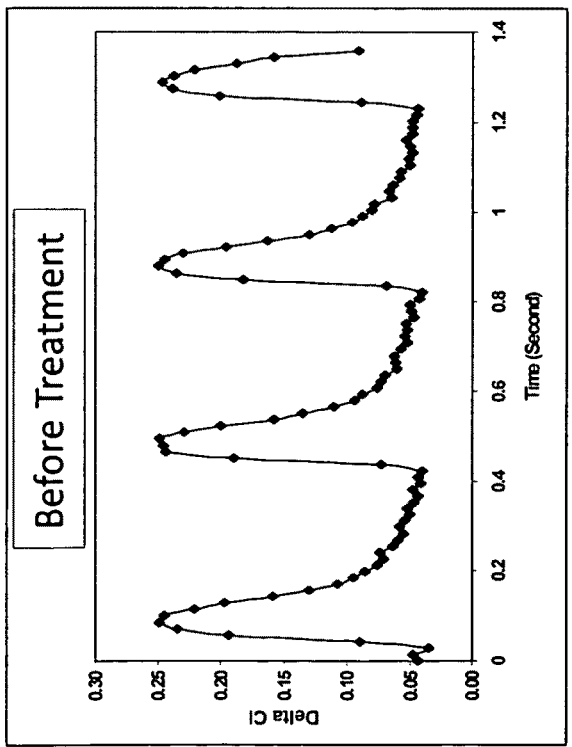
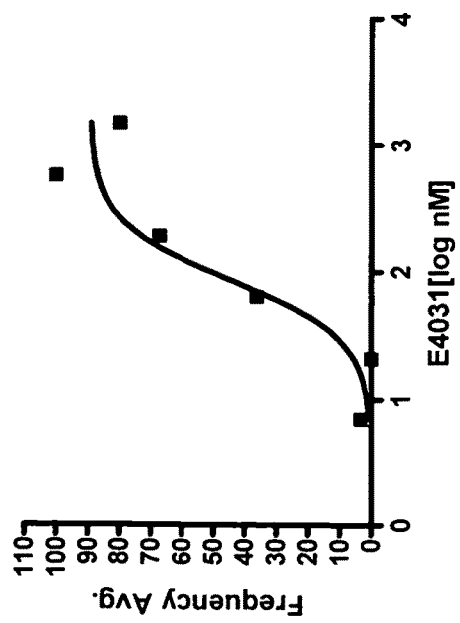
FIG. 3

| Hours Post Cultivatio n (hrs) | Beating Pattern | Beating Frequency (1/min ± SD) N=8 | Amplitude (Delta CI) N=8 | Beat Duration (ms) | Time to Max (Tr) (ms) | Decay Time(Td) (ms) |
|---|---|---|---|---|---|---|
| | 500 ms | | | | | |
| 12 | | NA | NA | NA | NA | NA |
| 24 | | NA | NA | NA | NA | NA |
| 48 | | 80 ± 5.7 | 0.14 ± 0.003 | 142 ± 4.6 | 38 ± 1.4 | 124 ± 12.0 |
| 72 | | 145 ± 2.7 | 0.24 ± 0.005 | 98 ± 3.0 | 29 ± 5.1 | 88 ± 7.2 |
| 96 | | 127 ± 2.8 | 0.33 ± 0.007 | 105 ± 2.4 | 31 ± 3.3 | 97 ± 6.4 |

| | Normalized Beating Rate (IC50; M) | Normalized Amplitude (IC50; M) | Beat Duration (IC50; M) | Beat Rate Irregularity (IC50; M) |
|---|---|---|---|---|
| Isradapine | $19.7 \times 10^{-9}$ M | $42.3 \times 10^{-9}$ M | N.A. | N.A. |
| (S)-(-)-Bay K8644 | $77.3 \times 10^{-9}$ M | N.A. | N.A. | $24.2 \times 10^{-9}$ M |
| Chromanol 293B | $2.9 \times 10^{-5}$ M | $2.8 \times 10^{-5}$ M | N.A. | $3.0 \times 10^{-5}$ M |
| E4031 | $26.9 \times 10^{-9}$ M | N.A. | $2.4 \times 10^{-7}$ M | $56.6 \times 10^{-9}$ M |
| TTX | $2.8 \times 10^{-7}$ M | $5.3 \times 10^{-8}$ M | N.A. | N.A. |
| Isoproterenol | $1.4 \times 10^{-8}$ M | N.A. | $7.1 \times 10^{-9}$ M | N.A. |
| Carbachol | $1.7 \times 10^{-7}$ M | $1.2 \times 10^{-6}$ M | N.A. | N.A. |

FIG. 12

| Compound | LOC | RTCA Beating Pattern |
|---|---|---|
| DMSO | NA | |
| Astemizole | 0.1 uM | |
| Amitriptyline hydroch | 10 uM | |
| Amiodarone | 0.1 uM | |
| Bepridil | 10 uM | |
| Bretylium | 10 uM | |
| Clofilium | 0.1 uM | |
| Chlorpheniramine | 10 uM | |
| Cisapride | 1 uM | |
| Chloroquine | 10 uM | |
| Chlorpromazine | 10 uM | |

FIG. 15

| Compound | LOC | RTCA Beating Pattern |
|---|---|---|
| DMSO | NA |  |
| Domperidone | 0.1 uM |  |
| Droperidol | 1 uM |  |
| Diltiazem hydrochloride | 1 uM | 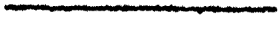 |
| 4,4'-Diisothiocyanatostilbene-2,2'-disulfonic acid disodium salt | 10 uM |  |
| Diphenhydramine hydrochloride | 10 uM | 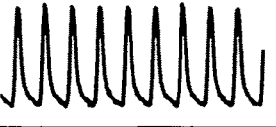 |
| Desipramine hydrochloride | 10 uM |  |
| 5,5-Diphenylhydantoin | 10 uM |  |
| Disopyramide | 10 uM | 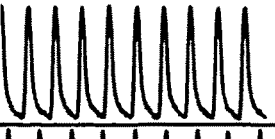 |
| Felbamate | 10 uM | 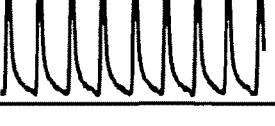 |
| Fluoxetine hydrochloride | 10 uM | 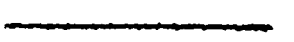 |
FIG. 15 (con't)

| Compound | LOC | RTCA Beating Pattern |
|---|---|---|
| DMSO | NA |  |
| FK-506 | 10 uM |  |
| Flecainide acetate | 10 uM | 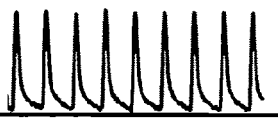 |
| Fexofenadine hydrochloride | 10 uM | 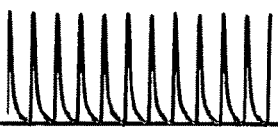 |
| Haloperidol | 1 uM |  |
| Indapamide | 10 uM |  |
| Isradipine | 10 nM |  |
| Imipramine hydrochloride | 100 nM |  |
| Ketoconazole | 10 uM | 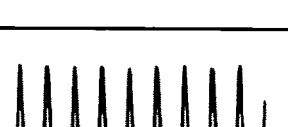 |
| Lidocaine | 10 uM | 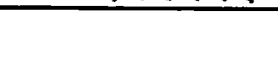 |
| Loratadine | 10 uM | 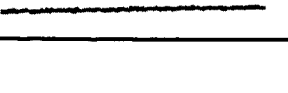 |
FIG. 15 (con't)

| Compound | LOC | RTCA Beating Pattern |
|---|---|---|
| DMSO | NA | |
| Mefloquine hydrochloride | 1 uM | |
| Mexiletene hydrochloride | 1 uM | |
| Mesoridazine benzenesulfonate | 1 uM | |
| (±)-Metoprolol (+)-tartrate | 10 uM | |
| Mibefradil dihydrochloride | 1 uM | |
| Nicardipine hydrochloride | 1 uM | |
| (±)-Norverapamil hydrochloride | 10 uM | |
| F2-Terfenadine | 1 uM | |
| Paroxetine maleate | 100 nM | |
| Pimozide | 100 nM | |

FIG. 15 (con't)

| Compound | LOC | RTCA Beating Pattern |
|---|---|---|
| DMSO | NA | 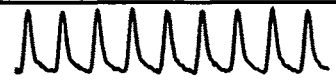 |
| PD-118057 | 10 uM | 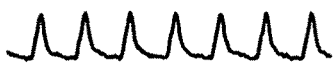 |
| Sodium phosphonoformate tribasic hexahydrate | 10 uM | 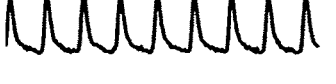 |
| Paroxetine hydrochloride hemihydrate (MW = 374.83) | 10 uM | 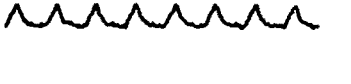 |
| Quinidine | 10 uM | 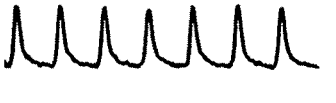 |
| (±)-Sotalol hydrochloride | 1 uM | 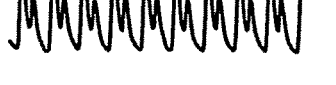 |
| Salmeterol xinafoate | 1 uM | 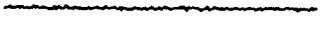 |
| Sertraline hydrochloride | 1 uM | 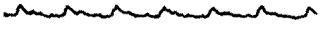 |
| Tamoxifen | 10 uM |  |
| Tizanidine hydrochloride | 10 uM | 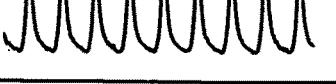 |
| Thioridazine hydrochloride | 10 uM | 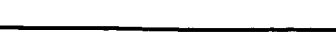 |
FIG. 15 (con't)

DATA ANALYSIS OF IMPEDANCE-BASED CARDIOMYOCYTE-BEATING SIGNALS AS DETECTED ON REAL-TIME CELL ANALYSIS (RTCA) CARDIO INSTRUMENTS

CROSS-REFERENCE TO RELATED APPLICATIONS

This invention is a continuation in part of U.S. patent application Ser. No. 12/435,569, filed on May 5, 2009, which claims benefit of priority to U.S. patent application Ser. No. 61/191,684, filed on Sep. 11, 2008 and U.S. provisional patent application Ser. No. 61/126,533, filed on May 5, 2008, the contents of each are herein incorporated by reference in their entirety.

This application also claims benefit of priority to U.S. patent application Ser. No. 61/345,867 filed on May 18, 2010; the contents of which are herein incorporated by reference in their entirety.

TECHNICAL FIELD

The invention relates to cell based assays and their use for monitoring cardiomyocyte beating and more specifically to methods for determining cardiomyocyte beating parameters and their use to identify compounds having potential cardiotoxic effects.

BACKGROUND OF THE INVENTION

Cardiac safety pharmacology is the study of the potential undesirable pharmacodynamic effects of a substance on heart function in relation to exposure to the substance in the therapeutic range and above. Cardiac safety is a major concern in current drug development. Since 1981, at least 10 blockbuster drugs have been withdrawn from the market due to cardiac liability, defined as potentially undesirable effects on heart function. Furthermore, cardiac safety is a major reason for late stage attrition of drug candidates during development.

There are three non-mutually exclusive ways that non-cardiac drugs may lead to cardiac liability. Directly, cardio-toxic drugs are drugs which cause damage via necrosis or apoptosis, such as anthracyclines. Pro-arrhythmic drugs are drugs which induce arrhythmia. Indirectly, cardiotoxic drugs are drugs which indirectly affect cardiac function, such as by causing narrowing of the arteries.

Directly, cardiotoxic drugs directly affect the viability of cardiomyocytes and therefore heart function. A prominent class of drugs in this category is chemotherapeutic drugs, such as anthracyclines. Mortality due to cardiac disease is thought to be 8-fold higher for survivors of childhood cancers who have received chemotherapy. These drugs are thought to disrupt iron metabolism, generating harmful oxygen radical species which ultimately cause mitochondrial damage and apoptosis.

Pro-arrhythmic drugs induce arrhythmia. Normal synchronized contractile activity of cardiomyocytes is the result of orchestrated ion currents passing across the cell membrane via ion-specific channels and coupling with the specialized cytoskeleton. Disturbances in the ionic movement of interference with ion channel activities may lead to arrhythmia. It is believed that one of the primary targets of pro-arrhythmic drugs is the ERG channel, which is responsible for delayed repolarization of cardiomyocytes. ERG channel blockage may lead to QT elongation and this may cause a fatal form of ventricular arrhythmia called Torsades de Pointes (TdP). Between 1990 and 2006, 10 blockbuster drugs have been withdrawn from the market due to induction of TdP. The drugs that have been associated with cardiac arrhythmia and removed from the market are prenylamine, terodiline, sparfloxacin, sertindole, terfenadine, astemizole, grepafloxacin, cisapride, droperidol, and levacetylmethadol.

Excitation-contraction coupling (ECC) is a term used to describe the physiological process of converting an electrical stimulus to a mechanical response. The process is fundamental to muscle physiology, wherein the electrical stimulus may be an action potential and the mechanical response is in the form of contraction. Although ECC has been known generally over half a century, it is still an active area of biomedical research.

Cardiomyocytes are specialized muscle cells of the myocardium that are capable of excitation-contraction coupling. Cardiomyocytes are commonly used in biomedical research to assess the cardiotoxicity of potential drugs or treatments. Two conventional approaches to assess cardiotoxicity are primarily used. A first approach involves isolation of cardiomyocytes directly from a mammalian species such as rats and dogs followed by electrophysiological studies on the isolated cardiomyocytes. However, this approach suffers from being extremely labor-intensive, time consuming and costly and at the same time not very amenable to the high throughput demands of pharmaceutical industry. An alternative approach utilizes cell-based assay models, which heterologously express specific ion channels such as hERG channels or voltage-gated calcium channels. These cardiac ion channels have been envisioned as possible molecular targets through which drugs could induce cytotoxicity. These cell-based systems allow assessment of drug-channel interaction by monitoring the effect of the drug on currents produced by different channels in cultured cells using a technique known as "patch clamping." Patch clamping isolates regions of the cell membrane containing channel proteins and measures changes in electrical potential difference. However, use of this method in high throughput requires automation of patch clamping in an array format with reliable giga seal, which even though is becoming increasing available, is not yet widespread. In addition, cardiac toxicity may occur by other mechanisms that could be possibly missed by this type of targeted approach.

An alternative to in vitro ion-channel recording assays as well as the labor-intensive isolation of primary tissue is the differentiation of embryonic stem (ES) cells into cardiomyocytes. The utility of ES cells as a treatment for various chronic diseases has received much attention in recent years. Mammalian ES cells are self renewing cells derived from the inner cell mass of a blastocyst stage embryo which can be differentiated into multiple different cell types. It has been demonstrated that the mouse ES cells as well as human ES cells can be differentiated into cardiomyocytes which retain the ability to beat in culture. Differentiation of ES cells first involves an intermediate in vitro developmental stage in which ES cells form compact cell structures known as embryoid bodies. These embryoid bodies can induce the developmental program of ES cell differentiation into multiple cell types including cardiomyocytes, which are distinguished in culture by their ability to undergo spontaneous beating. These ES derived in vitro differentiated cardiomyocytes recapitulates the normal development of cardiomyocytes as evidenced by the stage-specific expression of cardiomyocyte specific genes. All the known transcription factors, ion channels and structural proteins that are part of normal heart development and function in vivo are also expressed in ES-derived cardiomyocytes.

Even though high throughput to medium throughput systems have been developed for functional characterization of cell lines heterologously expressing the gene for specific ion channels, high throughput techniques for functional characterization of more complex systems such as cardiomyocytes have been limited. Technologies designed to assess cardiomyocyte behaviour and function and the effect of drugs and other manipulations in vitro can be divided into two different approaches. One approach involves long term assessment of cardiomyocyte viability for example in response to certain compounds. Such assays are typically end point assays designed to measure a cellular component such as ATP which correlates with the degree of viability of the cells. The other approach involves studying short term effect of drugs and compounds on beating function of cardiomyocytes. High throughput techniques for short term functional characterization of ion channels and other targets in cardiomyocytes has been rather challenging and limited. The available systems typically only monitor a single cardiomyocyte or a small number of cardiomyocytes at a time with very limited throughput.

SUMMARY OF THE INVENTION

The invention addresses the need for further study of cardiomyocytes and their response to therapeutic agents by establishing a number beating parameters which may be used to assess the heath, function and response of the cardiomyocytes to potential treatment of drugs or chemical compounds. The above is accomplished by providing a method of determining one or more beating parameters for use in cardiomyocyte beating analysis. The method includes providing a cell analysis device including wells, each well including a sensor capable of monitoring beating of cardiomyoctes in millisecond time resolution; adding cardiomyocytes to the wells; monitoring the beating of the cardiomyocytes in millisecond time resolution to obtain a plurality of beating measurements; and calculating one or more beating parameters from the plurality of beating measurements.

The cell analysis device should be able to measure cardiomyocytes beating in millisecond time resolution. In some embodiments, the cell analysis device is an impedance monitoring device, such as an impedance monitoring device having a sensor formed from two electrode structures, each having substantially the same surface area. In other embodiments, the sensor is an optical sensor. Examples of suitable optical sensors are those that can be used to detect or measure changes in cell morphology, cell adhesion and cell number. Among these include a resonant waveguide or a resonant waveguide grating sensor.

In some embodiments, beating measurements are plotted over time to form, at least in part a beating curve. Beating parameters can then be derived from the curve or corresponding data. Among the beating parameters of particular interest, include beating rate, beating amplitude, rising time, falling time, beating period, IBD50, IBD10, IBD90, rising slope, falling slope, normalized beating rate, normalized beating amplitude, beating pattern similarity and beating rhythm irregularity.

Test compounds may be added to identify changes in beating parameters and thus the effect on cardiomyocytes. Accordingly, in some embodiments a test compound is added to the wells at a number of different concentrations and a dose response curve (DRC) is constructed. In further embodiments, the methods include determining an IC50 or EC50 value from the dose response curve. In other embodiments a test compound is added to the wells to assess a potential difference in beating parameters, which may be indicative of cardiotoxicity.

BRIEF DESCRIPTION OF THE DRAWINGS

FIG. 1A shows a nonconductive substrate 101 with 16 electrode arrays or sensors fabricated on the substrate. Each electrode array 102 includes two electrode structures. Each electrode structure comprises multiple electrode elements. Each electrode array connects to two electrical traces 103, with each of the two traces connected one of the two electrode structures. These electrical connection traces 103 from the electrode array 102 are connected to the connection pads 104 at the edges of the substrate 101. As shown in FIG. 1A, each of the four electrode arrays in each of four quarters on the substrate 101 have one of their electrical connection traces 103 connected to a common connection pad 104. Thus, for the depicted device there are four common connection pads 104, one for each quarter of the device. In addition, each electrode array has a separate electrical connection trace 103, connecting to an independent connection pad 104. Thus, there are total 20 connection pads 104 at the edges of the substrate (101). In FIG. 1B a single exemplary electrode array or sensor is shown. The electrode array has two electrode structures, where each electrode structure comprises multiple electrode elements 105 shown here having a circle-on-line geometry. In this electrode array structure, electrode elements 105 of one electrode structure of the array alternate with electrode elements 105 of the other electrode structure of the array. Each of the electrode structures is independently connected to its electrode bus 106, in this case, by means of direct connection of the electrode elements 105 to the electrode bus 106. Each electrode bus 106 forms an arc around the perimeter of the array, where the two buses of the array do not abut or overlap. The electrically conductive connection traces 103 in FIG. 1A connect each bus with a connection pad 104 in FIG. 1A on the edge of the substrate 101 in FIG. 1A.

FIG. 3 depicts graphs showing change in cell index in millisecond time resolution before and after adding 190 nM of compound E4031, which is has pro-arrhythmic effects.

FIG. 9A shows long term impedance monitoring of cells with arrows depicting time points for short term millisecond recording. FIG. 9B shows beating activity and profile of mESCC at time points identified in FIG. 9A after cell seeding. The beating rate (1/min), amplitude (delta CI), beat duration (IBD50; ms), Time to Max (ms) and Decay Time (ms) were quantified using the RTCA Cardio software and as described in the Examples section. The data represents the average of 8 wells −/+Standard Deviation. A total duration of 5 sec recording time is displayed. FIG. 9C demonstrates blebbistatin, an inhibitor of myosin heavy chain ATPase activity, inhibits beating activity of mESCC, which is restored by washing out the compound and replacing by normal growth media. FIG. 9D demonstrates that Blebibistain treatment of mESCC has no effect on field potential recording as measured on Multi-Electrode Arrays.

FIG. 10A shows results from treatment with Isrdapine, an L-Type voltage-gated calcium channel inhibitor, FIG. 10B shows results from treatment with (S)-(−)Bay K 8644, an agonist of L-Type voltage-gated calcium channels, FIG. 10C shows results from treatment with chromanol, inhibitor of the slow delayed rectifier $K^+$ current.

FIG. 11A shows results from treatment with E4031, an inhibitor of ERG type $K^+$ channel, FIG. 11B shows results from treatment with Tetrodotoxin (TTX), inhibitor of voltage-gated $Na^+$ channel, and FIG. 11C shows results from treatment with isoproterenol, an ionotropic agent and agonist of the (3-adrenergic receptor.

FIG. 12 depicts a table summarizing beating parameters including normalized beating rate, normalized amplitude and beating rate irregularity of the compounds tested in FIGS. 10A-C and FIGS. 11A-C.

FIG. 13A shows screening, in a dose-response manner in mESCC, 4 drugs which have been withdrawn from the market due to increased incidence of TdP arrhythmia. For each compound a total of 5 sec of beating activity is displayed. For Astemizole, cisapride, droperide and sertindole the dose-response profiles are shown at 30 min, 15 min, 180 min and 165 min after compound addition, respectively. The bottom row shows the dose-response for each of the compounds at the indicated time points based on calculation of beat duration parameter as described in the Examples section.

FIG. 14A shows mESCC treated with increasing concentrations of doxorubicin. Dose-dependent impedance-based cellular profiles were monitored for up to 24 hours after compound treatment. In FIG. 14B a total of 5 sec of recording is shown for each dose at the given time point. The beating activity is quantified in terms of beating rate and displayed in each box. In FIG. 14C mESCC were seeded in the wells of E-PLATE (ACEA Biosciences, San Diego, Calif.) and on day 3 treated with 20 μM Pentamidine. The beating activity was monitored at the indicated time windows after compound treatment and quantified based on beat duration as mentioned in the Examples section.

FIG. 15 depicts a table summarizing the screening results of 50 compounds with potential cardiotoxic liability screened at 3 final doses (10 μM, 1 μM and 0.1 μM) using the RTCA Cardio system together with mESCC. For each compound both the lowest observed concentration (LOC) which resulted in an effect on mESCC and the resulting beating profile was included.

DETAILED DESCRIPTION

Figure 1A:
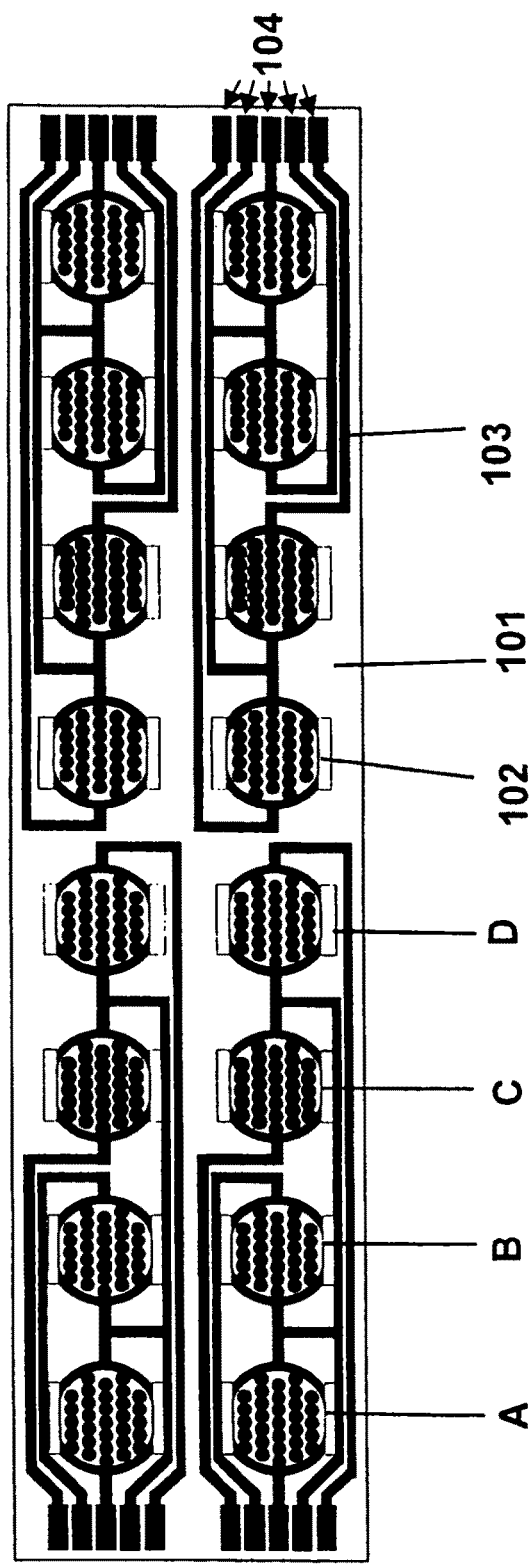
FIGS. 1A-B depict schematic drawings of one design of a cell-substrate impedance measurement device of the present invention.
Figure 1B:
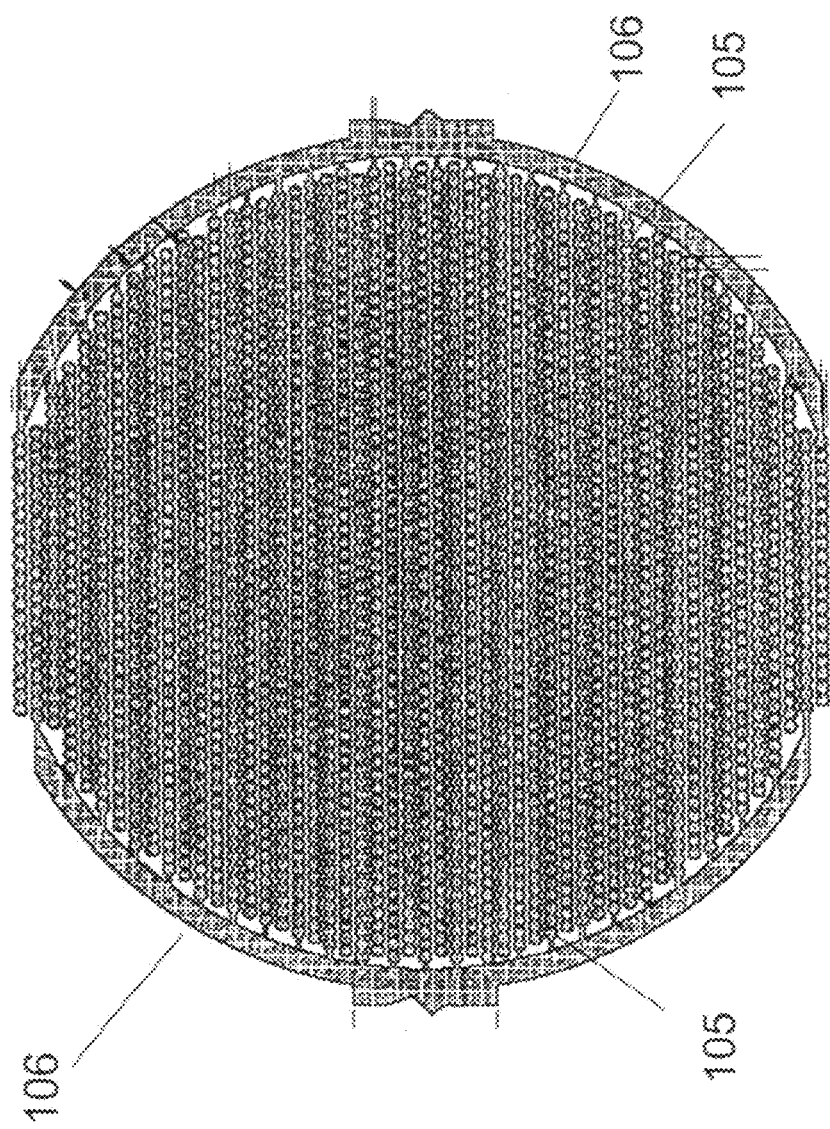
Figure 2:
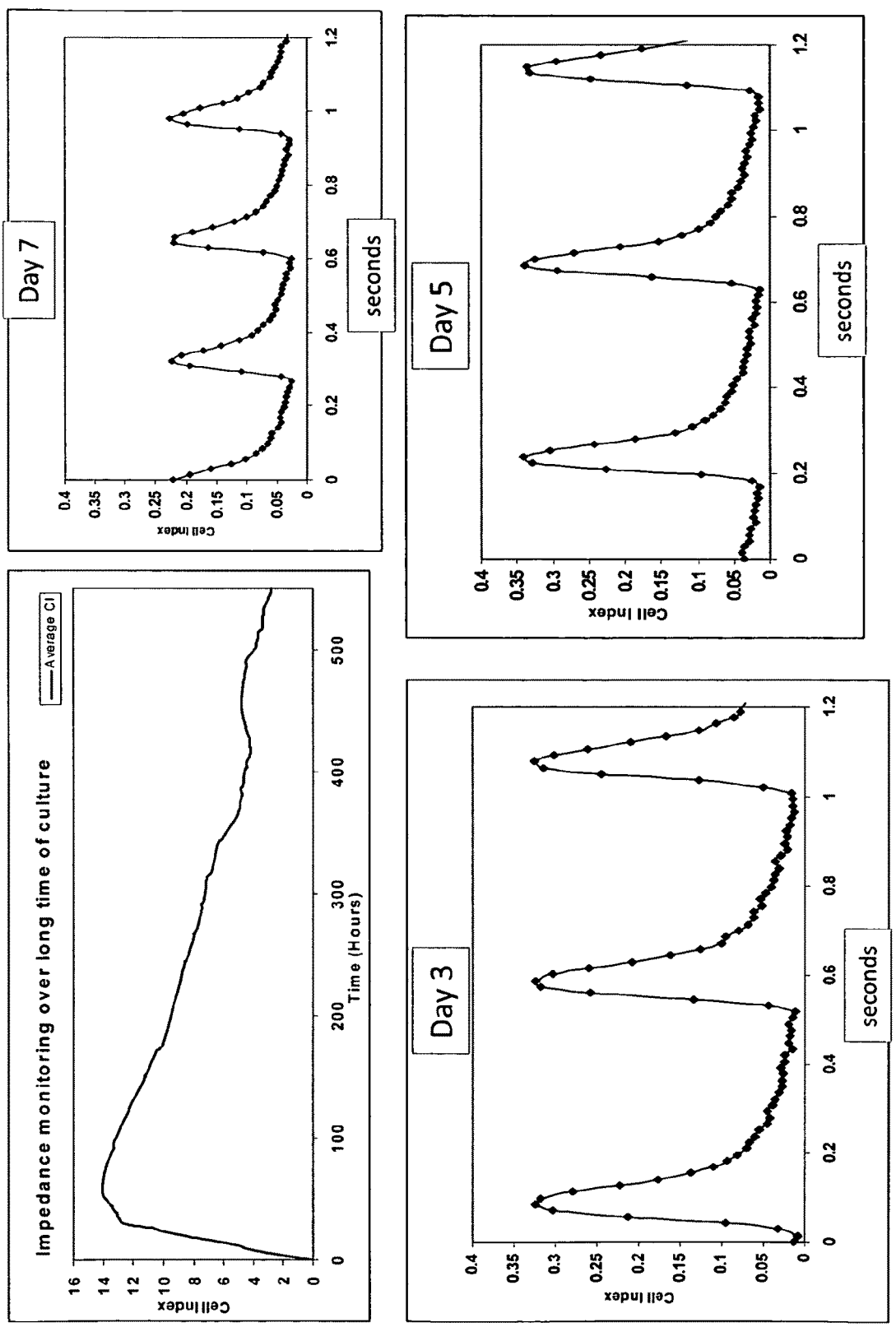
FIG. 2 depicts graphs demonstrating combined long term and short term measurement of cardiomyocytes beating over at least 7 days including measurement in millisecond time resolution with corresponding cell index values calculated from impedance measurements over beating periods at days 3, 5 and 7.
Figure 4:
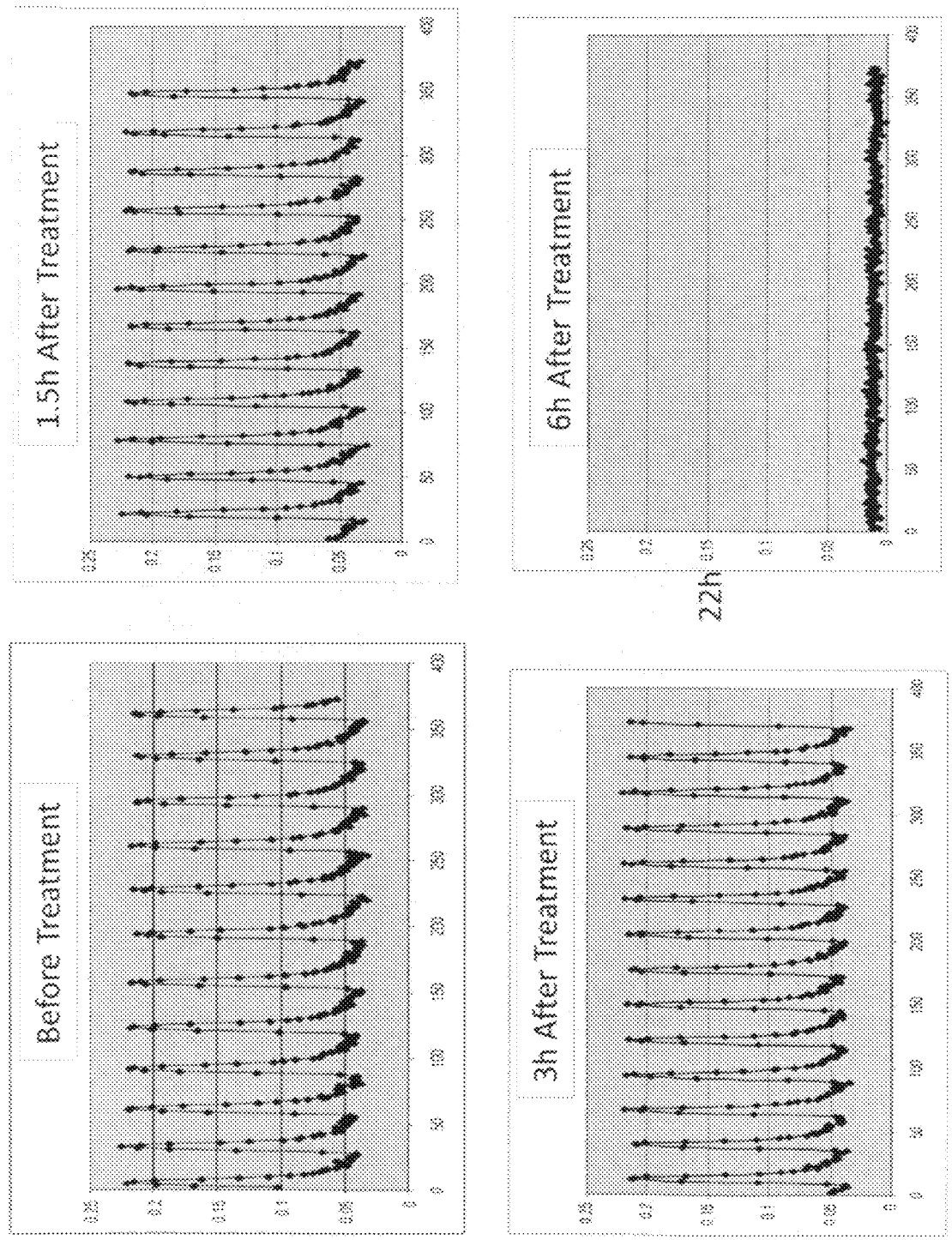
FIG. 4 depicts a series of graphs showing the effect on cell index of a cardiomyocyte cell population in millisecond time resolution before and after adding petamidine, which prevents ERG transport to the membrane and thus a delayed adverse effect over 6 hours.
Figure 5:
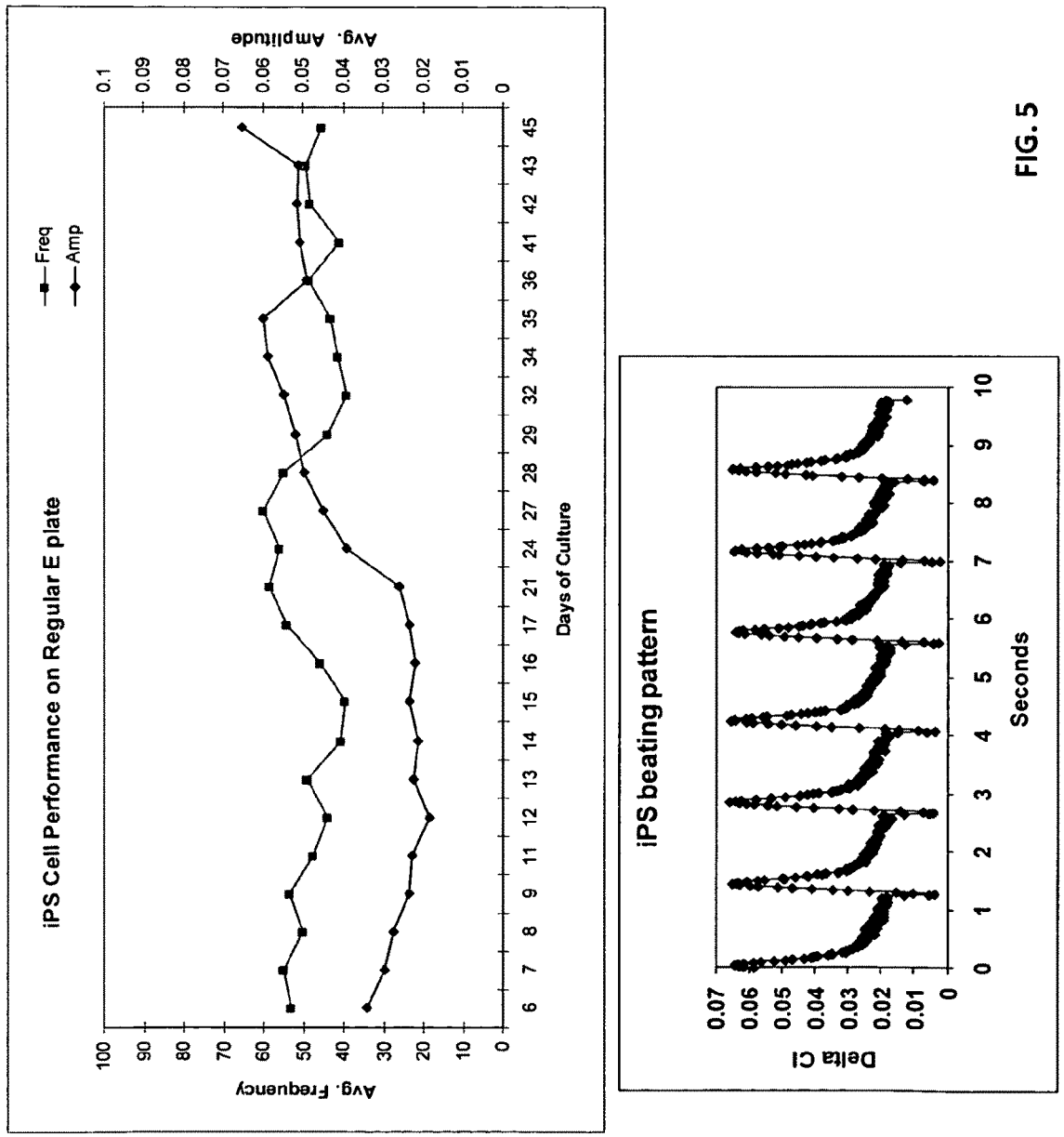
FIG. 5 depicts a series of graphs showing change in cell index in millisecond time resolution of iPS cell-derived cardiomyocytes and monitoring of the cardiomyocytes over 45 days.
Figure 6:
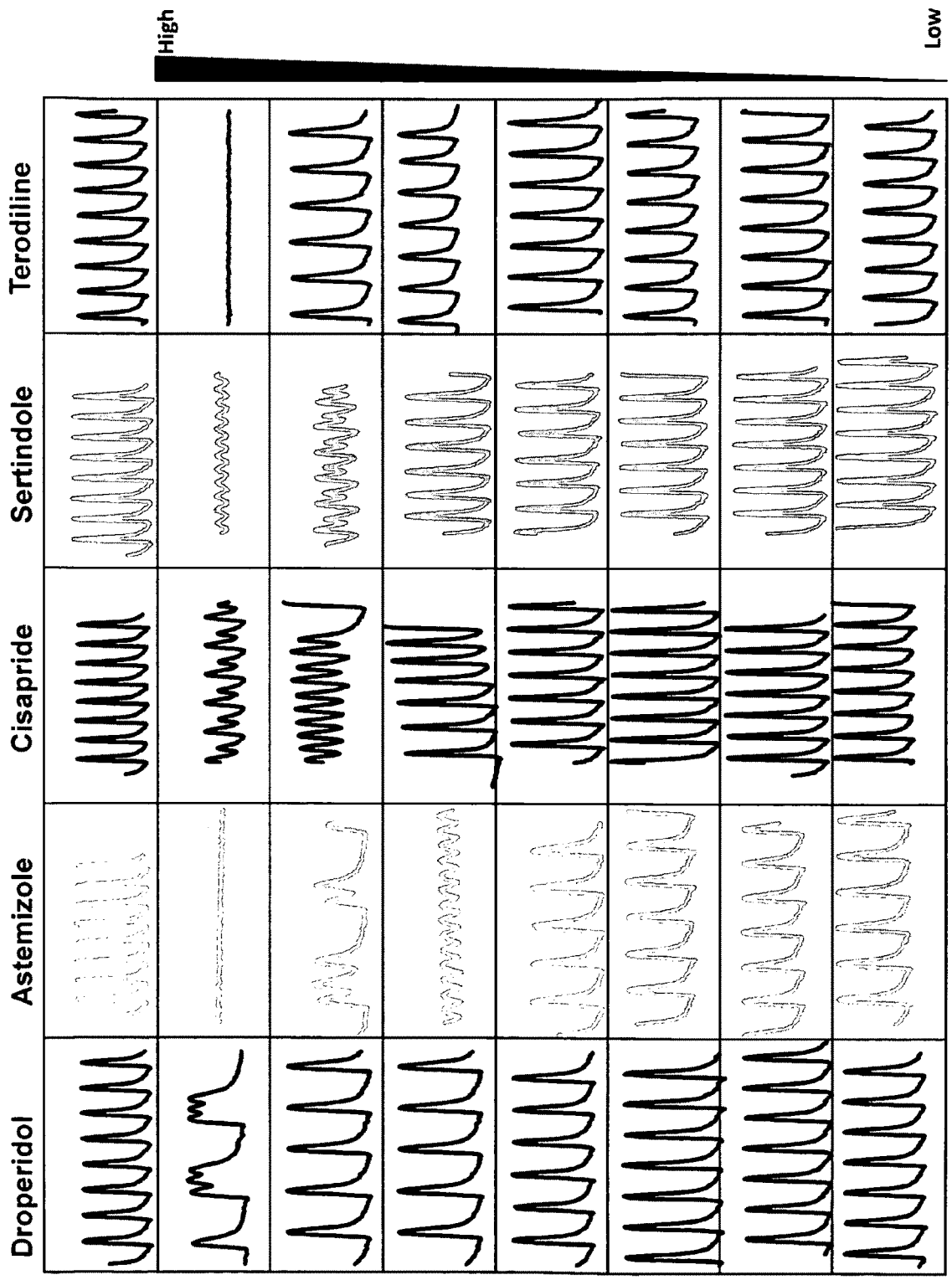
FIG. 6 depicts millisecond time resolution charting of cell index of cardiomyocytes tested with increasing concentration of pro-arrhythmic drugs withdrawn from the US market, namely Droperidol, Astemizole, Cisapride, Sertindole and Terodiline.

The present invention addresses the need to provide methods to further improve monitoring of excitation-contraction coupling in cardiomyocytes and excitable cells, such as for cardiac safety assessment and for the study of cardimyocyte function and differentiation. Specifically, embodiments of the invention describe label-free methods for monitoring cardiomyocytes in vitro and methods for effective comparison by establishing a plurality of beating parameters. The methods are capable of continuously monitoring excitation-contraction coupling and determining the beating parameters in a relatively high-throughput manner, which offers a unique approach to assessing the safety of potentially cardiotoxic treatments, which may not be readily apparent. The systems and methods can be used to assess both short term and long term effects of substances on cardiomyocyte beating, viability and morphology.

Monitoring Beating of Cardiomyocytes

While the invention relates primarily to methods for determining beating parameters for beating analysis and comparison, it is important to obtain reliable beating measurements in millisecond time resolution. Millisecond time resolution preferably refers to the measurement or acquisition of data from at least two consecutive time points within 100 milliseconds of one another. More preferably, the at least two consecutive beating measurements are performed in less than 40 milliseconds. Still more preferably, the at least two consecutive measurements are performed in less than 20 milliseconds. In still further embodiments the at least two consecutive beating measurements are performed in less 10 milliseconds.

In one approach a device for monitoring the beating of cells may be an optical-based system, which uses an optical sensor. Optical sensors typically measure an optical property of the cell, which may relate cell morphology, cell adhesion degree and/or cell number. Among the optical sensors that may be used include resonant waveguide sensors or resonant wave guide grating sensors. For example, the resonant wave guide grating sensor utilizes the resonant coupling of light into a waveguide through a diffraction grating. A polarized light, covering a range of incident wavelengths, is directly used to illuminate the waveguide; light at specific wavelengths is coupled into and propagates along the waveguide. The resonance wavelength at which a maximum in coupling efficiency is achieved is a function of the local refractive index at or near the sensor surface. When the cardiomyocytes are cultured and attached to the surfaces of the resonant wave guide sensor, the local refractive index on the sensor/cell interface would be affected by changes in cell morphology, cell adhesion and other cellular properties. For example, a relocation or re-arrangement of certain cellular contents such as the change in cell adhesion degree, or membrane refilling, recruitment of intracellular proteins to activated receptors at the cell surface, or receptor endocytosis, the change in cell morphology may all result in the change in local refractive index, leading to a detectable change or shift in the maximum in coupling efficiency wavelength. The effect of the presence of the cells on a resonant wave guide grating sensor has been explored based on the dynamic mass redistribution model. The details of such optical sensors and other optical sensors for cell-based assays have been described in detail in "Label-free cell-based assays with optical biosensors in drug discovery", by Ye Fang, in Assay and Drug Development Technologies, Vol 4, pp 583-595, 2006. An optical-sensor based system may include a device comprising optical sensors in wells suitable for cell culture, an optical signal measurement/detection system such as optical CCD camera, an optical-signal processing algorithm to process optical signals in short-time resolution, such as millisecond resolution, to provide a cardiomyocyte-beating dependent curve, and to quantify cell beating and to derive cell-beating parameters (such as calculating average rate of beats per unit time, average amplitude intensity in a unit time as well as the average length of time between the beats) based on cell morphology images.

In the preferred approach the system is an impedance-based cell monitoring system. Most preferably, the system provides a device for monitoring cell-substrate impedance, an impedance analyzer capable of impedance measurements at millisecond time resolution, electronic circuitry that can engage the device and selectively connect two or more sensors or electrode arrays of the device to the impedance analyzer and a software program that controls the electronic circuitry and records and analyzes data obtained from the impedance analyzer. By providing the impedance based system with millisecond time resolution, beating measurements from excitation-contraction coupling of cells can be efficiently monitored in millisecond time resolution. Thus the methods provided herein may be combined with impedance-based systems to identify and evaluate changes in excitation-contraction events and shifts in beating parameters discussed below, which may be used for high throughput analysis of potential therapeutics. The skilled artisan will appreciate that millisecond time resolution measurements may be coupled with longer term impedance monitoring, such as longer than seconds, hours or days. In some embodiments, long term impedance monitoring is performed with intermittent periods of impedance monitoring at millisecond time resolution. Suitable impedance monitoring systems are described in detail in U.S. patent application Ser. No. 12/435,569, which is herein incorporated by reference in its entirety. A preferred electrode array or configuration is also provided in FIGS. 1A and B.

The preferred device for monitoring substrate impedance includes a nonconductive substrate having one or more individually addressable electrode arrays or sensors fabricated thereon and one or more wells. A surface of the substrate may be suitable for cell attachment, wherein the cell attachment results in a detectable change in impedance between electrodes within the array. Preferably, the nonconducting substrate is planar, and is flat or approximately flat. The substrates may be constructed from a variety of non-conductive materials known in the present art, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate is biocompatible with excitable cells such as cardiomyocytes; however, materials that are not biocompatible can be made biocompatible by coating with a suitable material, such as a biocompatible polymer or coating. Further, attachment or growth along the substrate or electrodes may be enhanced by pre-coating the substrate with a protein or compound that facilitates attachment or growth. Such compounds may be chosen according to techniques known in the cellular biology arts; however, in some embodiments fibronectin is effective. Alternatively, the substrate may be chemically modified to display reactive groups that enhance cell attachment, particularly ES cells or cardiomyocytes.

Preferably, each sensor or electrode array includes two or more electrode structures that are constructed to have dimensions and spacing such that they can, when connected to a signal source, operate as a unit to generate an electrical field in the region of spaces around the electrode structures. Preferably the electric field is substantially uniform across the array. An electrode structure refers to a single electrode, particularly one with a complex structure. Specifically, an electrode array includes two electrode structures, each of which includes multiple electrode elements, or substructures, which branch from the electrode structure. In preferred embodiments, the electrode structures of each of the two or more electrode arrays of a device have substantially the same surface area.

Each of the two electrode structures of an electrode array is connected to a separate connection pad that is preferably located at the edge of the substrate. Specifically, for each of the two or more electrode arrays of the device, preferably the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time using switches (such as electronic switches).

Preferably, each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array do not differ by more than 30%. More preferably, the electrode resistance at a first location on an array of the device and the electrode resistance at a second location on the same array do not differ by more than 15%. Even more preferably, the electrode resistance at a first location on an array of the device and a second location on the same array do not differ by more than 5%. More preferably yet, the electrode resistance at a first location on an array of the device and a second location on the same array do not differ by more than 2%.

Preferred arrangements for electrode elements and gaps between the electrodes and electrode buses in a given electrode array are used to allow all cells, no matter where they land and attach to the electrode surfaces and to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Preferably, devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structure. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in U.S. Pat. No. 7,470,533, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. Pat. No. 7,470,533, herein incorporated by reference for all description and disclosure of the design, features, and manufacture of impedance device comprising electrode arrays.

Descriptions of electrode arrays used for impedance measurement that apply to the devices of the present invention are also described in U.S. Pat. No. 7,470,533, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure. Electrode arrays may be provided in configurations, such as interdigitated, circle-on-line, diamond-on-line, concentric, sinusoidal and castellated.

Preferably, the electrode elements (or electrode structures) of an array of the present device of the present invention are of approximately equal widths. Preferably the electrode elements (or electrode structures) of an array of the present device of the present invention are greater than 20 microns and less than 500 microns in width, more preferably from about 50 to about 300 microns in width.

Preferably, the electrode elements (or electrode structures) of an array of the present device of the present invention are approximately evenly spaced. Preferably, the gap between electrode elements (or electrode structures) of an array of the present device of the present invention is less than 100 microns and more than 5 microns in width, more preferably from about 10 to about 80 microns in width.

Preferably, the device includes one or more fluid-impermeable receptacles which serve as fluid containers or wells. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastic, glass, or plastic coated materials such as a ceramic, glass, metal, etc. Descriptions and disclosure of devices that comprise fluid containers can be found in U.S. Pat. No. 7,470,533, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in U.S. Pat. No. 7,470,533, and also in U.S. Pat. No. 7,192,752, both herein incorporated by reference for disclosure of multiwell impedance measurement devices, including their design, composition, and manufacture. A device of the present invention preferably has between 2 and 1,536 wells and more preferably between 4 and 384 wells. In some embodiments the device includes 6 wells, 16 wells, 32 wells, 96 wells or 386 wells.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

In the system for monitoring impedance of beating cells the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 1 ohm and $10^3$ ohm in frequency range of 1.00 Hz to 300 kHz.

In preferred embodiments the impedance analyzer is capable of impedance measurements at millisecond time resolution. The required or desired time resolution may vary depending on the excitation cycle of the excitable cell. Excitable cells having shorter excitation cycles would tend to require faster time resolution. In some embodiments 500 millisecond time resolution is sufficient, such that at least two consecutive impedance measurements are between about 300 milliseconds and about 500 milliseconds apart. In preferred embodiments, impedance measurement at millisecond time resolution includes at least two consecutive impedance measurements less than 100 milliseconds apart. In some instances the at least two consecutive impedance measurements are less than 50 milliseconds or less than 40 milliseconds apart. In some instances the at least two consecutive impedance measurements are less than 20 milliseconds apart. In some instances at least two consecutive impedance measurements are less than 10 milliseconds apart. In some instances millisecond time resolution includes two consecutive impedance measurements between 1 millisecond and 5 milliseconds, between 5 milliseconds and 10 milliseconds, between 10 milliseconds and 20 milliseconds, between 20 milliseconds and 40 milliseconds, or between 40 milliseconds and 50 milliseconds apart. In some instances millisecond time resolution includes at least two consecutive impedance measurements between 50 milliseconds and 100 milliseconds apart. In some instances millisecond time resolution includes at least two consecutive impedance measurements between 100 milliseconds and 150 milliseconds or between 150 and 300 milliseconds apart.

With millisecond time resolution for impedance measurement, it becomes possible to resolve individual beating cycles of cardiomyocytes cultured on electrodes. Whilst theoretically one needs at least two data points for each beating cycle, in practice more than 2 data points are needed for each beating cycle. For example, if cells have a beating rate of 60 beats per minute, i.e, one beat per second. It would be preferred to have a time resolution of at least 200 milliseconds so that each beating cycle consists of 5 data points. More preferably, the measurement time resolution is 100 milliseconds. Still more preferably, the time resolution is 50 milliseconds or less.

One skilled in the art will understand that the cell-substrate impedance measurement or monitoring system with millisecond time resolution can be used to efficiently and simultaneously perform multiple assays by using circuitry of the device station to digitally switch from recording from measuring impedance over an array in one well to measuring impedance over an array in another well. Similarly, groups of wells may be monitored simultaneously and switched between designated groups. In one embodiment of the above system, the system under software control is capable of completing an impedance measurement for an individual well at a single frequency within milliseconds, such as less than 100 milliseconds, less than 40 milliseconds, less than 20 milliseconds, less than 10 milliseconds or between 1 millisecond and 40 milliseconds. In some embodiments the user may choose the frequency of measurement for millisecond time resolution.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. In one embodiment of the above system, the multi-well device takes the form of a specialized microtiter plate which has microelectronic sensor arrays integrated into the bottom of the wells.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes. Further, by using millisecond time resolution differences in impedance may be detected or monitored that relate to excitation-contraction coupling, including the beating of cardiomyocytes or stem cells differentiating into cardiomyocytes, and the signaling between neurological cells. Impedance monitoring of the excitation cycle of excitable cells may be determined and monitored before, during or after adding a test compound, which is suspected of affecting the excitation cycle. Thus, by monitoring the excitation cycle of the excitable cell before, during or after adding a test compound the system provides data corresponding to the potential affect of the compound on the cardiovascular system, the heart, the nervous system, and the like. In some embodiments monitoring the excitation cycle of the cell before, during or after adding a compound provides cardiotoxicity data useful in drug screening.

In some embodiments a device station or electromechanical apparatus or assembly capable of interfacing multiwell devices can include one or more platforms or one or more slots for positioning one or more multiwell devices. The one or more platforms or one or more slots can comprise sockets, pins or other devices for electrically connecting the device to the device station. The device station or electromechanical apparatus or assembly capable of interfacing multiwell devices preferably can be positioned in a tissue culture incubator during cell impedance measurement assays. It can be electrically connected to an impedance analyzer and computer that are preferably located outside the tissue culture incubator.

The device station or electromechanical apparatus or assembly capable of interfacing multiwell devices includes electronic circuitry that can connect to the impedance monitoring device and an impedance analyzer and electronic switches that can switch on and off connections to each of the two or more electrode arrays of the multiwell devices used in the system. The switches of the device station or electromechanical apparatus or assembly capable of interfacing multiwell devices are controlled by a software program, each of which has been improved to provide millisecond time resolution. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored using at least two time points. The device station can connect individual arrays of a device to an impedance analyzer to monitor one, some, or all of the arrays of a device for a measurement time point. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc. Further, since a plurality of beating parameters are obtained using the beating measurements, software provides menus to select one or more of the beating parameters for analysis.

The software, termed RTCA CARDIO SOFTWARE (ACEA Biosciences Inc., San Diego, Calif.), also permits fast analysis of beating parameters. Thus, after obtaining impedance measurements the software can calculate or determine from the impedance measurement a plurality of beating parameters such as beating rate, beating amplitude, rising time, falling time, beating period, IBD10, IBD50, IBD90, rising slope, falling slope, normalized beating rate, normalized beating amplitude, beating pattern similarity and beating rhythm irregularity, and perform subsequent statistics, such as average and standard deviation and further supply IC50 or EC50 values for dose-response testing.

Determining Cell Index from Impedance or Optical Measurements

Although raw impedance values or raw values obtained from optical sensors may be used as beating measurements in preferred embodiments the raw impedance values are converted to cell index values or delta cell index values for comparison or further derivation into beating parameters as discussed below. Information regarding how to calculate a cell index, cell change index, normalized cell index, and delta cell index may be found in U.S. patent application Ser. No. 12/435,569, U.S. patent application Ser. No. 11/903,454, and U.S. Pat. No. 7,470,533, the contents of which are herein incorporated by reference with respect to the cell index, cell index number, cell change index, and cell change index number. However a briefly summary is provided.

The cell index obtained for a given well reflects: 1) how many cells are attached to the electrode surfaces in this well, and 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes the cell index equals 0. A higher value of "cell index" or "cell number index" indicates that, for the same type of the cells and cells under similar physiological conditions, more cells are attached to the electrode surfaces. Thus cell index is a quantitative measure of cell number present in a well. A higher value of "cell index" may also indicate that, for the same type of the cells and the same number of the cells, cells are attached better (for example, cells spread out more, or cell adhesion to the electrode surfaces is stronger) on the electrode surfaces.

Non-limiting examples for determining cell index follow. Cell index can be calculated by: at each measured frequency, calculating the resistance ratio by dividing the measured resistance (when cells are attached to the electrodes) by the baseline resistance; finding or determining the maximum value in the resistance ratio over the frequency spectrum; and subtracting one from the maximum value in the resistance ratio. In another variation, cell index is determined by: at each measured frequency, calculating the resistance ratio by dividing the measured resistance (when cells are attached to the electrodes) to the baseline resistance; finding or determining the maximum value in the resistance ratio over the frequency spectrum; and taking a log-value (e.g., based on 10 or e=2.718) of the maximum value in the resistance ratio. In another variation, cell index is determined by: at each measured frequency, calculating the reactance ratio by dividing the measured reactance (when cells are attached to the electrodes) to the baseline reactance; finding or determining the maximum value in the reactance ratio over the frequency spectrum; and subtracting one from the maximum value in the resistance ratio. In still another variation, cell index can be calculated by: at each measured frequency, calculating the resistance ratio by dividing the measured resistance (when cells are attached to the electrodes) to the baseline resistance; then calculating the relative change in resistance in each measured frequency by subtracting one from the resistance ratio; and then integrating all the relative-change value.

It is worthwhile to point out that it is not necessary to derive such a "cell index" for utilizing the impedance information for monitoring cell conditions over the electrodes. Actually, one may choose to directly use impedance values (e.g., at a single fixed frequency; or at a maximum relative-change frequency, or at multiple frequencies) as an indicator of cell conditions.

A "normalized cell index" at a given time point is calculated by dividing the cell index at the time point by the cell index at a reference time point. Thus, the normalized cell index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

The time-dependent cellular response (including cardiotoxicity response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cardiotoxic responses) may be analyzed for their higher order derivatives with respect to time. Such high order derivatives may provide additional information as for how cells responding to different compounds and as for the mechanisms of compound action.

The use of cell index together with millisecond time resolution impedance monitoring is demonstrated in FIGS. 2-6, which depict high resolution images of the cardiomyocyte beating cycle and pattern shifting in response to administration of cardiotoxic compounds. While cell index permits graphically depicting the beating cycle, still more detailed analysis of beating parameters reveals improvements to cardiomyocyte population analysis.

Beating Parameters Derived from Millisecond Time Resolution Measurements or Cell Index While impedance measurements, optical measurements and cell index values can provide valuable information about a cell population, a variety of beating parameters are established which further assist in the analysis of a beating cardiomyocyte, a beating cell or cell population differentiating into a beating cell population. Further, the beating parameters permit comparisons before and after treatment with a compound, typically a test compound, to assess its effect or predicted effect on a cardiomyocyte cell population and the like. As such, the beating parameters may be used to establish or confirm safety of a compound or provide further insight as to the potential mechanism of action of a compound, such as its effect on stem cell differentiation to or away from a cardiomyocyte cell type or characteristic. Further, by providing a compound at various concentrations its dose response can be studied. The below beating parameters have been found useful in assessing potential effects on cardiomyocytes and thus each alone or in combination can be used to assess potential risk of compound based therapies.

Figure 7:
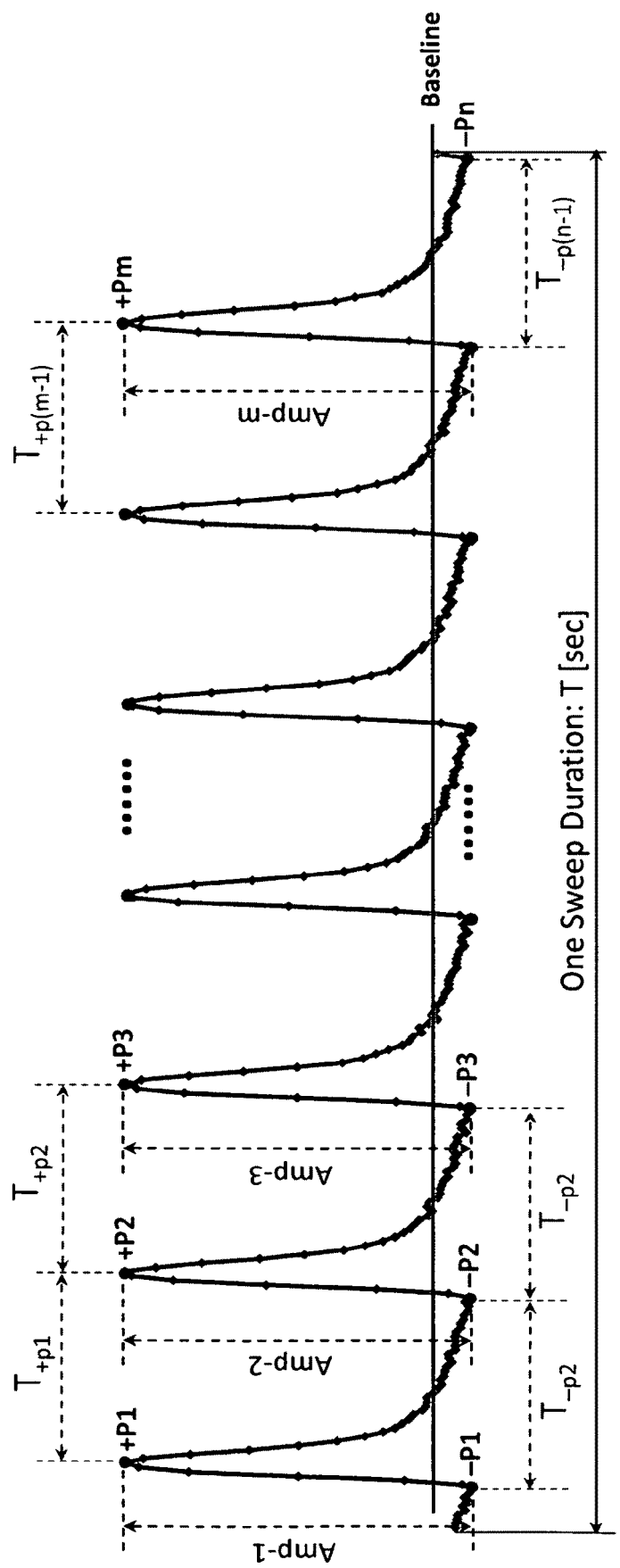
FIG. 7 depicts a graphical representation of multiple cardiomyocyte beating periods and graphical illustration of features used in beating parameters including positive peaks P1, P2, P3 . . . Pm; negative peaks −P1, −P2, −P3, . . . −Pm; and beating amplitude Amp-1, Amp-2, Amp-3 . . . Amp-m.

In one approach beating measurements are used to determine beating cycle peaks associated with a cell. Beating itself corresponds to the excitation-contraction coupling of the cells. Turning to FIG. 7, beatings are defined as a sequence of Positive Peaks (+P as labeled) and Negative Peaks (−P as labeled). The value of these Positive Peaks and Negative Peaks and the corresponding time periods determine the beating characteristics, which reveal the status of the cardiomyocyte population. For example, in FIG. 7, a Positive Peak may correspond to the contraction of cardiomyocytes, whilst the return of measurement values to baseline and to negative peak may correspond to the relaxation of cardiomyocytes.

As an example, time dependent impedance values or cell index values for a well are analyzed by deriving their first order derivatives and second order derivatives using numerical methods. The beating cycle peaks are those data points where the first order derivatives of impedance values or cell index values are zero or close to zero in absolute value. If the beating cycle peak is a positive peak (i.e. peak corresponds to a maximum value in measured impedance or cell index over the beating cycle), then the peak would correspond to data points where the second order derivatives of the impedance values or cell index values are negative and where the first order derivatives of the impedance values or cell index values are zero or close to zero in absolute value. If the beating cycle peak is a negative peak (i.e. peak corresponds to a minimum value in measured impedance or cell index over the beating cycle), then the peak would correspond to the data points where the second order derivatives of the impedance values or cell index values are positive and where the first order derivatives of the impedance values or cell index values are zero or close to zero in absolute value.

In yet another approach, the method for searching for and identifying "positive peaks" and "negative peaks" may involve the use and modification of various mathematical algorithms, e.g., the Douglas-Peucker algorithm. The Douglas-Peucker algorithm is an algorithm for reducing the number of points in a curve that is approximated by a series of points. Based on the required maximum distance between on the original curves and on the simplified curves, the Douglas-Peucker algorithm could also be adopted to identify positive peaks and negative peaks in time-dependent data point series for impedance values and/or cell index vales.

In another approach, a method of determining a beating cycle peak is to search for the data point where the trend of the data changes direction from "increasing" to "decreasing" with time (for a positive peak), or from "decreasing" to "increasing" (for a negative peak). After the identification of the beating cycle peaks, the impedance or cell index values at such peak time points provide the magnitude or amplitude of the beating cycle peaks.

After determining the beating cycle peaks, various methods can be used to calculate the beating rate. A beating rate parameter is generally provided as beatings per minute. In a positive peak counting approach, the number of positive peaks is determined over a given time interval and converted to the desired unit, preferably beats per minute. Similarly, in a negative peak counting approach the number of negative peaks is determined over given time interval and converted to the desired unit. As an example, if there are 2 peaks in a one second interval, then the beating rate would be 2 beats per second, or 120 beats per minute. In still another approach, beating rate is calculated by determining the time period between a series of two or more positive peaks or between a series of two or more negative peaks. That is, in this approach a unit of time (e.g., 1 minute) is divided by the time period between two adjacent peaks. For example, if two adjacent peaks are separated by 500 milliseconds, then the beating rate would be 120 beats per minute. In a time interval comprising multiple positive or negative peaks, the beating rate could be determined by the following method. Take positive peaks as an example, the time periods between every pairs of two adjacent positive peaks are calculated. Then the beating rate could be calculated in two ways. The first method is to divide a unit of time (e.g., 1 minute) by the average of the time periods between all two-adjacent positive peaks in the given time interval. The second method is to calculate the corresponding beating rates based on each pair of two adjacent positive peaks and then to average of the adjacent-peaks-derived beating rates.

To further assist in comparison, beating rates can also be normalized. Determining a normalized beating rate is achieved by dividing the beating rate at a selected data analysis time by a beating rate at a normalization time. Thus a beating rate identical to that at the normalization time would be defined as 1. Normalizing beating rates can provide a more clear indication of whether and to what degree a change in beating rate occurs. For example, normalization time corresponds to the time point of measurement immediately prior to a compound treatment of the cardiomyocytes. Thus, normalized beating rates could provide clear information as for what the effect of the compound has on the beating rates. A normalized beating rate close to 1 or equal to 1 means that the compound does not have much effect on the beating rate, A normalized beating rate smaller than 1 means that the compound may result in reduction in the beating rates of cardiomyocytes. A normalized beating rate larger than 1 means that the compound may cause an increase in the beating rates of cardiomyocytes. Normalized beating rates could be derived for beating rates calculated using different methods such as peak-counting derived beating rates and beating peak periods derived beating rates.

Beating amplitude is a parameter used in some embodiments to describe or correspond to the intensity of the peak, which may reflect the extent of contraction or relaxation of cardiomyocytes during a beating cycle. Determining beating amplitude can involve a whole peak approach, which could be determined by the difference between a negative peak and the following positive peak as shown in FIG. 7. For example, in FIG. 7 the beating amplitude is shown as the difference in cell index between a Negative Peak to the following adjacent Positive Peak (Amp-1, Amp-2, Amp-3, . . . , Amp-m). In another approach, beating amplitude for a positive peak is the difference between a determined baseline to a positive peak. In still another approach beating amplitude for a negative peak is the difference between a determined baseline to a negative peak. An exemplary baseline is shown in FIG. 7.

Thus, for a single beating cycle, one could define or identify different types of amplitude (or an amplitude) of the beating-cycle peaks, including the amplitude of positive peak, the amplitude of negative peak and the amplitude of the whole peak in a cycle. From the measured data point series, a baseline value, which may theoretically correspond to the value when the cardiomyocytes are at their fully relaxation status, could be determined or identified from the measured data values in a time series. The amplitude of a positive peak is the impedance value or cell index value or other measurement value at the positive-peak time point subtracted by the baseline value. The amplitude of a negative peak is the impedance value or cell index value or other measurement value at the negative-peak time point subtracted by the baseline value. The amplitude of whole peak is the difference in the impedance value or cell index value or other measurement value between positive-peak time point and negative-peak time point.

Whilst the above paragraph discusses different types of the amplitudes of a single beating cycle, for a time period including multiple beating cycles, one could determine the average and standard deviations (or standard errors) of the positive-peak amplitude, the negative-peak amplitude and whole-peak amplitude.

Beating amplitude can also be normalized as a normalized amplitude. A normalized amplitude is the amplitude at a selected data analysis time divided by the amplitude at the normalization time point. A beating amplitude identical to that at the normalization time would be defined as 1. Thus, the normalized amplitude reveals differences, such as an increase or decrease in the amplitude or intensity of a beat compared to a referenced amplitude. For example, normalization time corresponds to the time point of measurement immediately prior to a compound treatment of the cardiomyocytes. Thus, normalized beating amplitudes could provide clear information as for what the effect of the compound has on the beating amplitudes. A normalized beating amplitude close to 1 or equal to 1 means that the compound does not have much effect on the beating amplitude. A normalized beating amplitude smaller than 1 means that the compound may result in reduction in the beating amplitudes of cardiomyocytes. A normalized beating amplitude larger than 1 means that the compound may cause an increase in the beating rates of cardiomyocytes.

Normalized beating amplitude could be derived for all three types of beating amplitudes, i.e. positive-peak based amplitude, negative-peak based amplitude and whole-peak amplitude.

In some instances, it is more useful to consider a beating amplitude that is less than the difference between the positive peak and negative peak or baseline. For example, in may be desirable to consider a portion of the amplitude, such as a 10% amplitude, 20% amplitude, 50% amplitude, 80% amplitude, 90% amplitude and the like. This may be particularly preferred when assessing other parameters together with beating amplitude such as when considering a rising slope or an IBD10, IBD50, IBD90 and the like.

Figure 8:
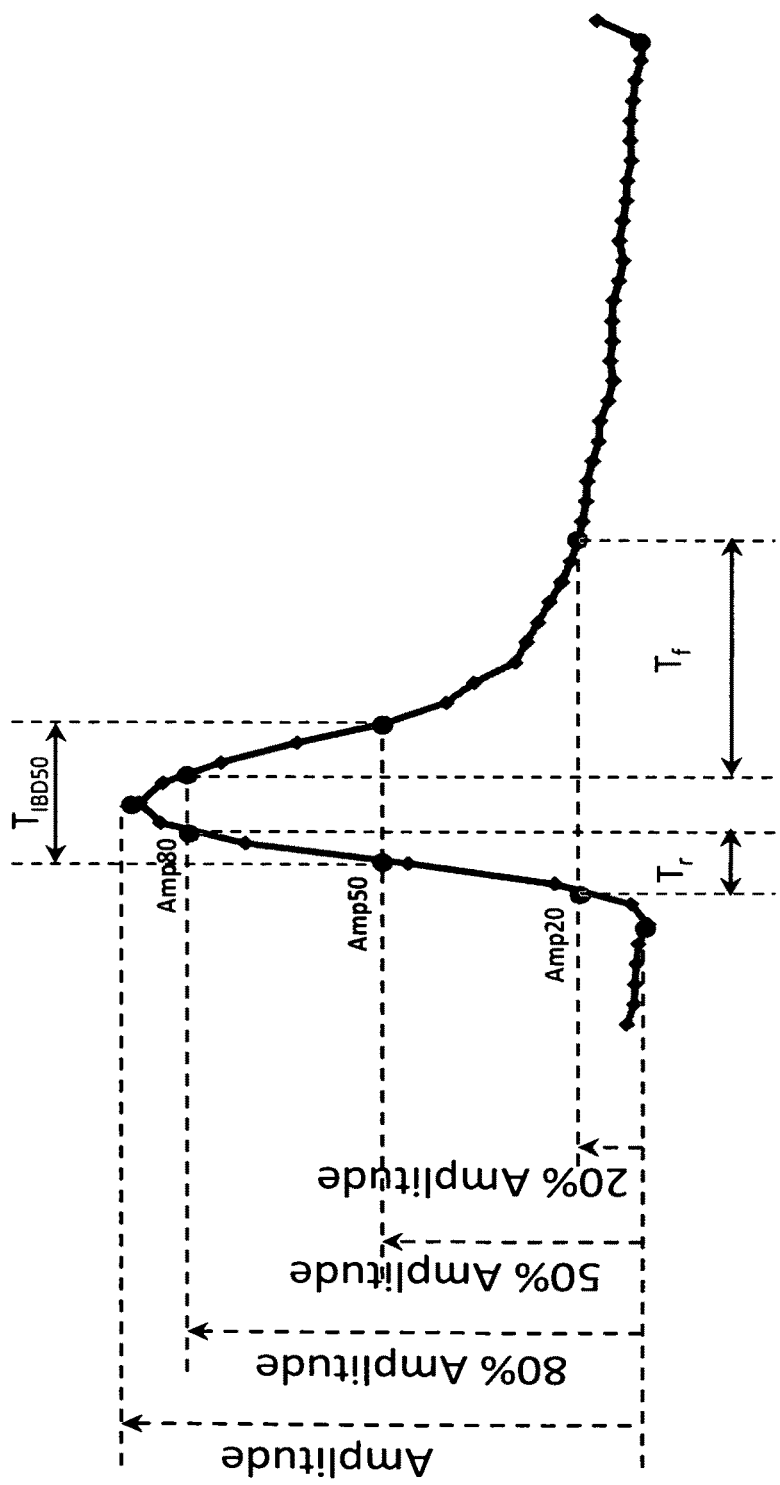
FIG. 8 depicts a graphical representation of a portion of a beating period to demonstrate a rise and fall of beating amplitude including time points for 20% amplitude, 50% amplitude and 80% amplitude.

Rising time $T_r$ is a parameter which provides the amount of time to travel the rising slope between the negative peak and the positive peak (or between the baseline and the positive peak). Typically, rising time is provided as an average over many beatings and is converted to time in the unit of seconds for analysis or comparison. In some embodiments rising time is calculated as the time needed to reach a positive peak or maximum amplitude from a negative peak or a baseline. Referring to FIG. 8 as an example, in other instances, rising time $T_r$ is calculated between data points positioned below the positive peak and above the negative peak (or below the positive peak and above the baseline). That is, since the slope of the beating curve changes dramatically at the peaks, it is often preferred to consider the rising time between 20% amplitude and 80% amplitude for comparison. Thus, when determining rising time it may be necessary to first determine the beating amplitude then determine suitable comparison points such as 20% amplitude, 50% amplitude, 80% amplitude and the like. By one example as illustrated in FIG. 8, rising slope can be calculated by the dividing the cell index change from 20% amplitude to 80% amplitude by the time it takes as follows:

Rising Slope=$(Amp_{80}-Amp_{20})/T_r$

Depending on specific application, it is possible that we may define other rising time and/or rising slopes, using different percentage amplitude points. For example, rising slope may be defined as:

Rising Slope=$(Amp_{90}-Amp_{10})/T_r$

Falling time $T_f$ is a beating parameter which provides the amount of time to travel the falling slope between a positive peak or a point of maximum amplitude to a negative peak or a baseline. Falling time $T_f$ can be provided as an average over many beatings and is generally converted to time in the unit of seconds for analysis or comparison. In some embodiments falling time $T_f$ is calculated as the time needed to reach a negative peak or baseline from a positive peak; however, referring again to FIG. 8 as an example, in other instances, falling time $T_f$ is calculated between data points positioned below the positive peak and above the negative peak. That is, since the slope of the beating curve changes dramatically at the peaks, it is often preferred to consider the falling time between 80% amplitude (or 90% amplitude) and 20% amplitude (or 10% amplitude) for comparison. Thus, when determining falling time it may be necessary to first determine the beating amplitude then determine suitable comparison points such as 10% amplitude, 20% amplitude, 50% amplitude, 80% amplitude, 90% amplitude and the like. By way of example, falling slope can be calculated by dividing the cell index change from 80% amplitude to 20% amplitude by the time it takes as follows:

Falling Slope=$(Amp_{80}-Amp_{20})/T_f$

Depending on specific application, it is possible that we may define other rising time and/or rising slopes, using different percentage amplitude points. For example, falling slope may be defined as:

Falling Slope=$(Amp_{90}-Amp_{10})/T_f$

IBD50 provides the time window between time points where the beating signals attains 50% amplitude. IBD50 is particularly useful when studying the effect of the compounds on the beating cycle of cardiomyocytes. For example, if a compound, through various mechanisms, results in prolongation of contraction phase of the beating cycle of the cardiomyocytes, then IBD50 derived from the beating cycle waveform may be increased as a result of the treatment of cardiomyocytes with this compound. In another example, if a compound results in certain pro-arrhythmia effects in cardiomyocytes (see FIG. 3 as an example where E4031 induced arrhythmia effects), then IBD50 derived from the beating cycle waveform may also be significantly altered. Similarly, other time windows can be used instead to assess similar pro-arrhythmia effects at different percentage of the amplitude such as 10% amplitude and 90% amplitude to give IBD10 and IBD90. Time between following IBD10, IBD50 or IBD90 measurements are designated as $T_{IBD10}$, $T_{IBD50}$, and $T_{IBD90}$. An exemplary $T_{IBD50}$ parameter is shown in FIG. 8.

Beating period (also referred to as "beating cycle") is a parameter which provides the time period between two positive peaks, two negative peaks or can be the time period between a positive peak and a negative peak. The beating period can be used to identify changes in beating rate or can be used as a defined period for comparison of other parameters, such as differences in amplitude, rising time, falling time and the like. In FIG. 7, within one Sweep Duration, the number of Positive Peaks is m (+P1, +P2, +P3, . . . , +Pm) and the number of Negative Peaks is n (−P1, −P2, −P3, . . . , −Pn). The time between two adjacent individual Positive Peaks (or/and two adjacent individual Negative Peaks) is defined as beating period. For example, the beating period based on the Positive Peaks is $T_{+P1}, T_{+P2}, \ldots, T_{+P(m-1)}$ and the beating period based on the Negative Peaks is $T_{-P1}, T_{-P2}, \ldots, T_{-P(n-1)}$.

Rising slope is a parameter corresponding to the slope that occurs during a specified time period when the measured impedance values or cell index values or other measurement/derived values increase with time. That is, the rising slope is a slope between a negative peak and an adjacent baseline point (which is after the negative peak in time), or between certain baseline point and an adjacent positive peak (which is after the baseline point in time), or between a negative peak and its immediately adjacent positive peak (which is after the negative peak in time). For a single beat, one could determine rising slopes based on different definitions as described in the previous sentence. The rising slope may be an average between multiple slopes across multiple beats.

Falling slope is a parameter that corresponds to the slope that occurs during a specified time period when the measured impedance values or cell index values or other measurement/derived values decrease with time. Thus, the falling slope is a slope between a positive and an adjacent baseline point (which is after the positive peak in time), or between certain baseline point and a negative peak (which is after the baseline point in time), or between a positive peak and its immediately adjacent negative peak (which is after the positive peak in time). For a single beat, one could determine falling slopes based on different definitions as described in the previous sentence. The falling slope may be an average between multiple slopes across multiple beats.

Beating pattern similarity is a parameter derived to quantify the degree of the similarity between the beating waveforms between two different time intervals. For any given time interval, the beating pattern is shown as the beating curves comprised of a number of measurement values (impedance values, cell index values or other values) across a number of time points during the time interval. Beating patterns at two time intervals may be compared numerically, such as by comparison between determined parameters for the beating curves at these two time intervals or patterns may be compared through the comparison of the beating curves. When comparing curves it may desirable to align curves to match an initial positive peak or initial negative peak. Aligning curves may also use a variety of curve algorithms, which identify distances or shifts between curves.

In one embodiment, the beating pattern similarity is derived as a parameter to compare the determined parameters for the beating curves at two time intervals. For example, one may compare the beating rates $BR_1$ and $BR_2$ at the two time intervals. An example of the beating pattern similarity is given as:

$$\text{Beating pattern similarity} = (2*BR_1*BR_2)/(BR_1*BR_1 + BR_2*BR_2)$$

With this above example, the beating pattern similarity is one (the highest value) when the beating rates at the two time intervals are the same. When the beatings rates differ at two time intervals, the beating pattern similarity would be less than 1. The more the beating rates differ, the smaller the beating pattern similarity value.

In a preferred embodiment, however, the beating pattern similarity is derived as a parameter to directly compare the beating curves at the two time intervals. The idea of the beating pattern similarity should possess such properties that the value for beating pattern similarity is large when the two beating curves are similar, and the value for beating pattern similarity is small when the two beating curves are not similar. There are multiple methods for deriving such beating pattern similarity values.

In one method, as briefly mentioned above, for comparing the beating curves at two time intervals (assuming the same measurement time resolutions for the measured data points), it may be desirable to align curves to match an initial positive peak or initial negative peak. After aligning the initial peaks, an "AND" operation is performed on the time points for the two beating curves so that the overlapping time points on the two beating curves are kept whilst non-overlapping time points on either one of the beating curves are discarded. Thus, the remaining, overlapping data points on the two beating curves are of the same number and it is possible to readily define a distance to describe whether the two beating curves are similar. For example, the beating pattern similarity could be the correlation coefficient between the two data series in the remaining portions of the two beating curves. Clearly, the more similar the two curves, the larger the correlation coefficient (i.e., the larger the beating pattern similarity value is). In another example, the beating pattern similarity could simply be certain mathematically-defined-distance (e.g. Euclidean distance) between two data series in the remaining portion of the two beating curves. Note that if the measurement time resolutions differ between the measured data points, additional time points may be artificially inserted into the beating curves with missing time points after mathematically interpolation of the values for such added time points based on other measured data points. With this operation, the two beating curves would have the same time resolutions.

In another method for comparing the beating curves at two time intervals (again, assuming the same measurement time resolutions for the measured data points), one would take the beating curve (out of the two) with the shorter time duration. If the time-shorter beating curve comprises more than half of the data points of the other beating curve, then some last data points from the shorter beating curve are removed to form a "base-curve" so that the number of the remaining data points in the shorter beating curve is half of the number of the data points in the other beating curve. Then a number of correlation coefficients would be determined where each correlation coefficient corresponds to the base-curve aligned to one continuous segment (comprising of the same data point number as the base-curve) of the other beating curve. For example, the first correlation coefficient is determined between the data series of the base curve and the data series of first half of the other beating curve (starting from the first data point). The second correlation coefficient is determined between the data series of the base curve and the data series from the other beating curve with starting point being the second data point. The last correlation coefficient is determined between the data series of the base curve and the data series from the second half of the other beating curve ending with the last data point. Finally, the beating pattern similarity is determined as the maximum value of all the correlation coefficients.

There may be other methods or algorithms that could be used for deriving beating pattern similarities. Beating pattern similarity could be used to analyze the effect of a compound on the beating pattern of cardiomyocytes. The beating curves from two time intervals are compared. For analyzing the effect of a compound, one time interval corresponds to the time period before compound treatment whilst the other time interval corresponds to the time period after compound treatment. The beating pattern similarity has an advantage over other parameters in comparing compound's effect on the cardiomyocytes. The advantage is that it could include or summarize all the effects due to the compound, i.e. the effects on the beating rates, beating waveform shapes or beating amplitudes etc could all be included into the single parameter of the beating pattern similarity.

Beating rhythm irregularity (BRI) is a parameter which identifies changes in beating rate or changes between peak periods for a beating curve over a time interval. Beating rhythm irregularity is also referred to as a beating rate irregularity index. If the beating rate or the beating peak period does not change with time, then the beating rhythm is regular and the parameter of the beating-rhythm-irregularity should be small, i.e. being zero or close to zero. On the other hand, if the beating rate or beating period does change with time, then beating rhythm is irregular and the parameter of the beating rhythm irregularity should have a large value. As one requirement, the parameter of the beating rhythm irregularity should be able to identify the arrhythmic beating of cardiomyocytes. Thus, the beating-rhythm-irregularity should attain a large value for the beating curves of cardiomyocytes if the cardiomyocytes exhibit arrhythmic beating. There are multiple methods for calculating the beating rhythm irregularity for a beating curve over a time interval. For example, the positive peak periods for each-adjacentpositive-peak-pair are calculated for the beating curve in the given time interval. Then the average and standard deviation of such multiple positive peak periods are calculated. The beating rhythm irregularity can be calculated by dividing the standard deviation of the positive peak periods by the average. In another example, the negative peak periods for each adjacent negative peak pair are calculated for the beating curve in the given time interval. Then the average and standard deviation of such multiple negative peak periods are calculated. The beating rhythm irregularity can be calculated by dividing the standard deviation of the negative peak periods by the average.

When the cardiomyocytes exhibit irregular beating, the beating curves may comprise some regular beating peaks (positive or negative) with regular amplitudes and some irregular beating peaks with somewhat smaller (/or larger) amplitudes or with somewhat different beating waveforms (e.g., the impedance value or cell index value or other measurement value does not return to baseline level after a beating peak). Thus, number or presence of the irregular positive (or negative) beating peaks could be used as an indicator for beating rhythm irregularity. Such regular and irregular beats can be determined and the ratio between the irregular and the regular beats, i.e. irregular to regular beats ratio, can be used to assess the pro-arrhythmia effects of the test compound. If there are no pro-arrhythmia effects, such ratio should be very small and close to zero.

The skilled artisan will appreciate compounds may be added to cardiomyocyte populations to test for potential changes or effects in beating parameters. Changes may include an increase or decrease in at least one of the beating parameters. The change may include an increase in beating rhythm irregularity if the compound causes an irregular beating in cardiomyocytes. If a compound results in a significant effect on the beating of cardiomyocytes, then beating pattern similarity between the beating curves before and after the compound treatment may be small.

In some instances beating measurements are continually monitored and a beating parameter is calculated for a single beating cycle within a time period for comparison. For example, the calculation for a beating parameter such as an amplitude can be performed for a single beating cycle. Further, a beating parameter from a single beating cycle (i.e. single beating peak) may provide a suitable control for later determined beating parameters. Due to the fact that single beating cycle may take a short time to complete, beating parameter for a single beating cycle (i.e. single beating peak) is sometimes referred as beating parameter at a single time point.

Frequently, it may be desirable analyze one or more parameters within a single beating period (i.e. for a single beating cycle). From a single beating cycle (single beating period) a variety of beating parameters can be assessed including beating amplitude, rising or falling time, rising and falling slope and IBD50 and the like. Consideration within a beating period may also be particularly useful for use as an initial beating period before the addition of a test compound to establish control beating data for later comparison. The single beating period approach may also be of interest if an irregularity is detected, such as an irregular positive peak, negative peak, slope between peaks and the like. For instance, an irregularity may be temporal and thus decay over time, which if limited to studying across multiple beating periods could be averaged out and thus not be identified as statistically significant. Thus, if such an irregularity is identified, analysis of the corresponding beating period may reveal significant differences compared to control. Still further, analysis of the single beating period may reveal a correlation to another change or shift in beating parameter not apparent through multi-beating period analysis.

In another approach one or more of the selected parameters are determined or calculated across a time period that includes multiple beating periods (i.e. multiple beating cycles). One or more parameters can be determined for each of the desired multiple beating periods. This approach may be used to monitor consistency over time or as a continuous scanning technique to identify potential periods of irregularity for further single beating period analysis. The approach may also be used to develop average values for comparison to test compounds.

While the methods permit the study of cardiomyocyte beating itself including, changes in beating in response to cardiomyocyte or stem cell differentiation and the like, the methods are also useful to assess the effect of one or more test compounds on a cardiomyocyte cell population. Such assays may help predict potential cardiotoxic effects of compounds, effect on cell differentiation or growth and the like. The skilled artisan will appreciate parameters for cell populations treated with test compounds may be compared to control treated populations, such as vehicle control, and the resulting parameters compared to assess for differences. Differences in beating parameters may be indicative of cardiotoxicity or other effects.

In another embodiment, a dose response curve (DRC) of a test compound is determined. A dose response curve reveals changes to beating parameters in response to difference in concentrations of test compound. Preferably, selected parameters are calculated from beating measurements that are measured from wells having different concentrations of the same test compound for a period of time where beating signals are continuous. Preferably, for each concentration, one value is calculated for the selected parameter for certain time points after addition of test compound. Then a concentration dependent dose response curve of the selected parameter is fitted to a non-linear, sigmoidal-dose-response equation to derive EC50 (or IC50) values. An example of a sigmoidal dose-response curve is as follows:

$$Y = \text{Bottom} + (\text{Top} - \text{Bottom})/(1 + 10^{(\text{Log } EC_{50} - X)})$$

An example of a sigmoidal dose-response with variable slop is as follows:

$$Y = \text{Bottom} + (\text{Top} - \text{Bottom})/(1 + 10^{((\text{Log } EC_{50} - X) * \text{HillSlope})})$$

The derived IC50/EC50 values for different compounds could be used to predict, analyze, or compare the different compounds' cardiotoxicity or different compounds' effect on beating of cardiomyocytes. Like IC50 or EC50 derived from other assays, a compound with lower IC50/EC50 values may indicate that the compound is more potent in inducing cardiotocixicity effect or causing an effect on beating of the cardiomyocytes than the compound with higher IC50/EC50 values.

To further demonstrate the use of the above parameters, modulators of ion channel and non-ion channel proteins and targets as well as modulators of neuro-hormonal machinery were tested in both time and dose-dependent manner (see for example FIGS. 3A-C and FIGS. 4A-C). Using various parameters such as beating rate, amplitude and IBD50, we have confirmed that the half maximal concentrations obtained for the different compounds are within the sensitivity range of patch clamp recording and other electrophysiological methodologies (data not shown). Importantly, we have also shown that certain classes of compounds such as blebbistatin, which serve to decouple excitation from contraction, can be missed by electrophysiological readouts but can be detected by the impedance-based measurement of cardiomyocyte beating. These observations demonstrate that impedance-based assay system can detect modulation of ion-channel and non-ion channel targets affecting both excitation and contraction of cardiomyocytes.

Figure 13A:
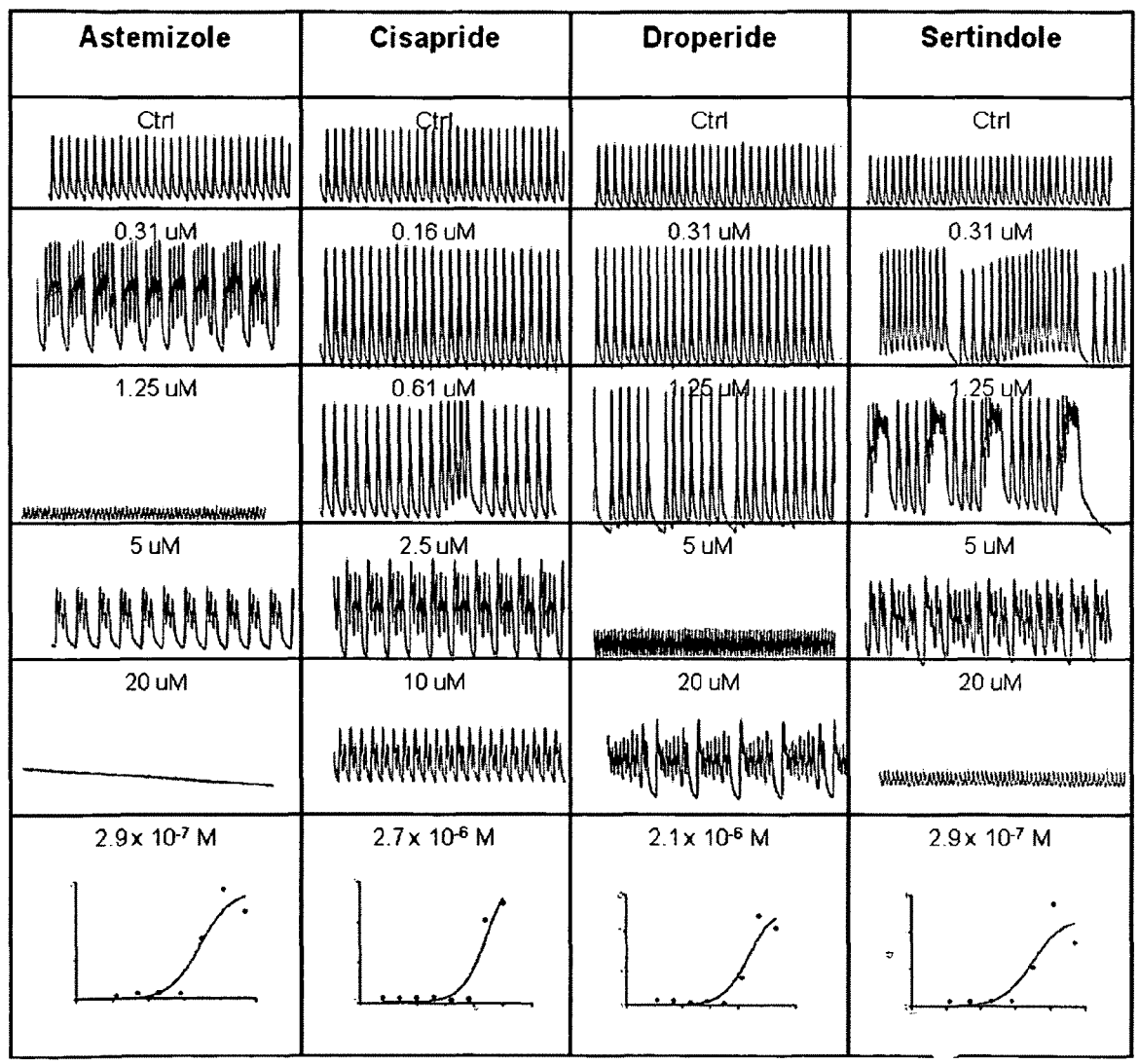
FIGS. 13A and B depict graphs showing mechanism-based cardiotoxicity profiling of cardiomyocytes using impedance-based devices.
Figure 13B:
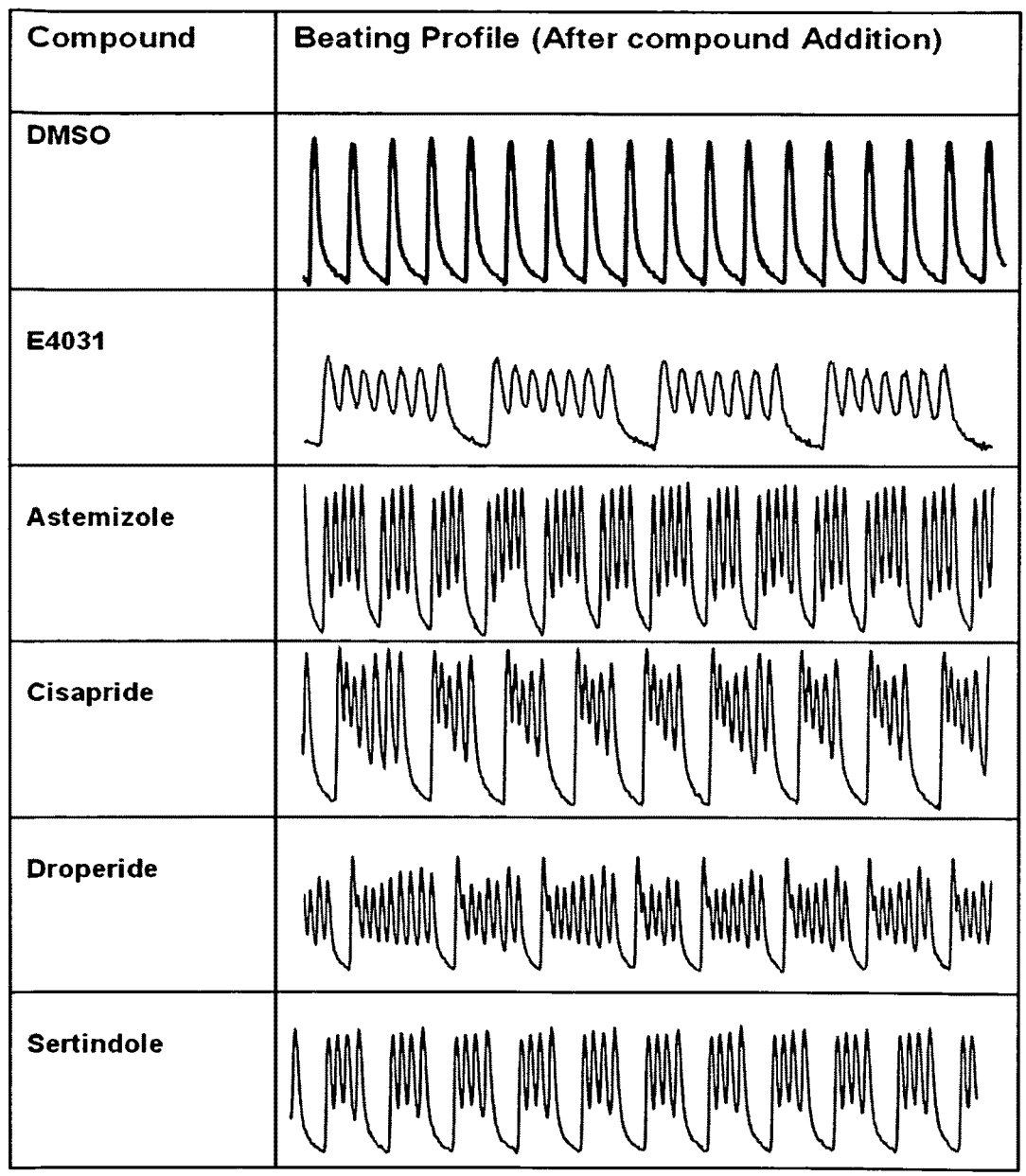
In FIG. 13B plateau oscillation profiles are induced by all four compounds tested in FIG. 13A as well as E-4031, indicating a common underlying mechanism; at total of 9 sec of beating profile recording is displayed for each of the compounds.

Also demonstrated is that a number of drugs that have been shown to induce ventricular arrhythmia in the clinic and subsequently withdrawn from the market display reproducible impedance-based signature beating profiles in a time and dose-dependent manner (FIGS. 13A-B and FIG. 15). These signature beating profiles are qualitatively similar to early after depolarization (EAD) phenomenon that is observed by manual patch clamp recording of cardiomyocytes after exposure to compounds and drugs that inhibit ERG channel activity and consequently $I_{kr}$ current (Fermini et al., 2003). While the appearance and mechanism of EADs are diverse, it is generally agreed that calcium homeostasis which can influence contraction plays an important role in various forms of EADs (Volders et al., 2000). It is thought that drug-induced block in $I_{kr}$ current can delay repolarization leading to delayed inactivation of calcium channels and consequently, the resulting late inflow of calcium contributes to emergence of EADs (Fermini et al., 2003). It is also important to mention that manifestation of arrhythmia by mechanisms other than ERG block and QT prolongation cannot be discounted. For example, it has been shown that certain compounds which shorten both APD and QT interval can also cause arrhythmia (Lu et al., 2008). While it remains to be shown whether such drugs can also induce characteristic EAD-like profiles in the assay system described here, it underscores the need for implementation of an assay system which can assess the integrated response of ion channel and non-ion channel targets to capture the full, range of drug responses.

Figures 14A, 14B:
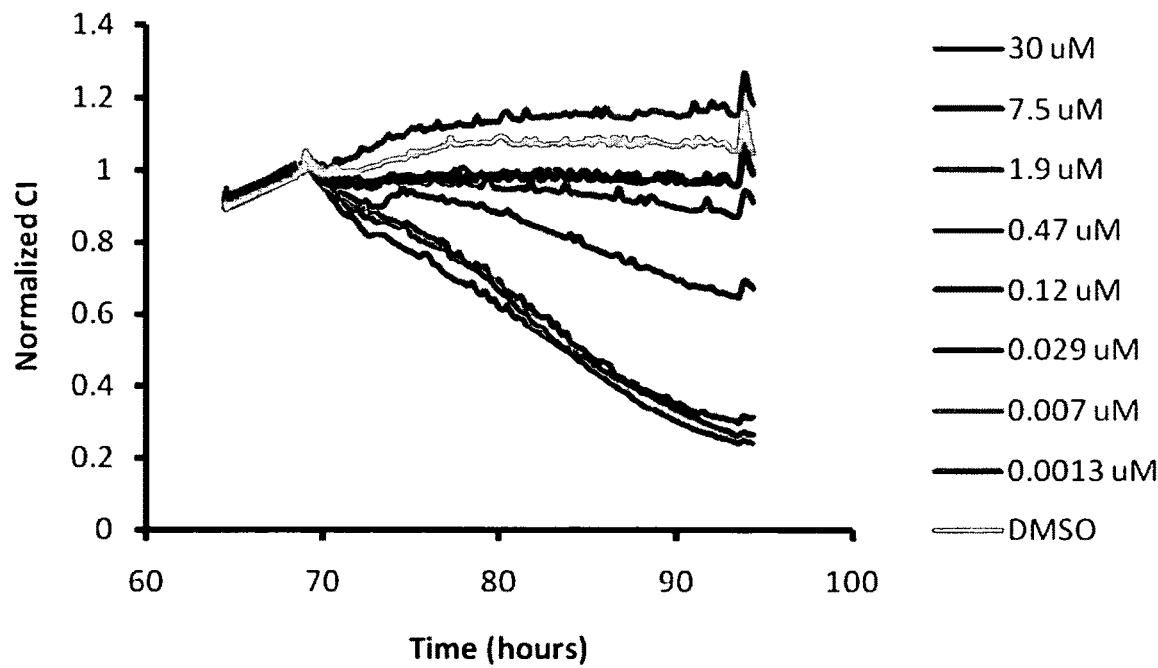
FIGS. 14A-C depict graphs and results from treatment with doxorubicin and pentamidine.
Figure 14C:
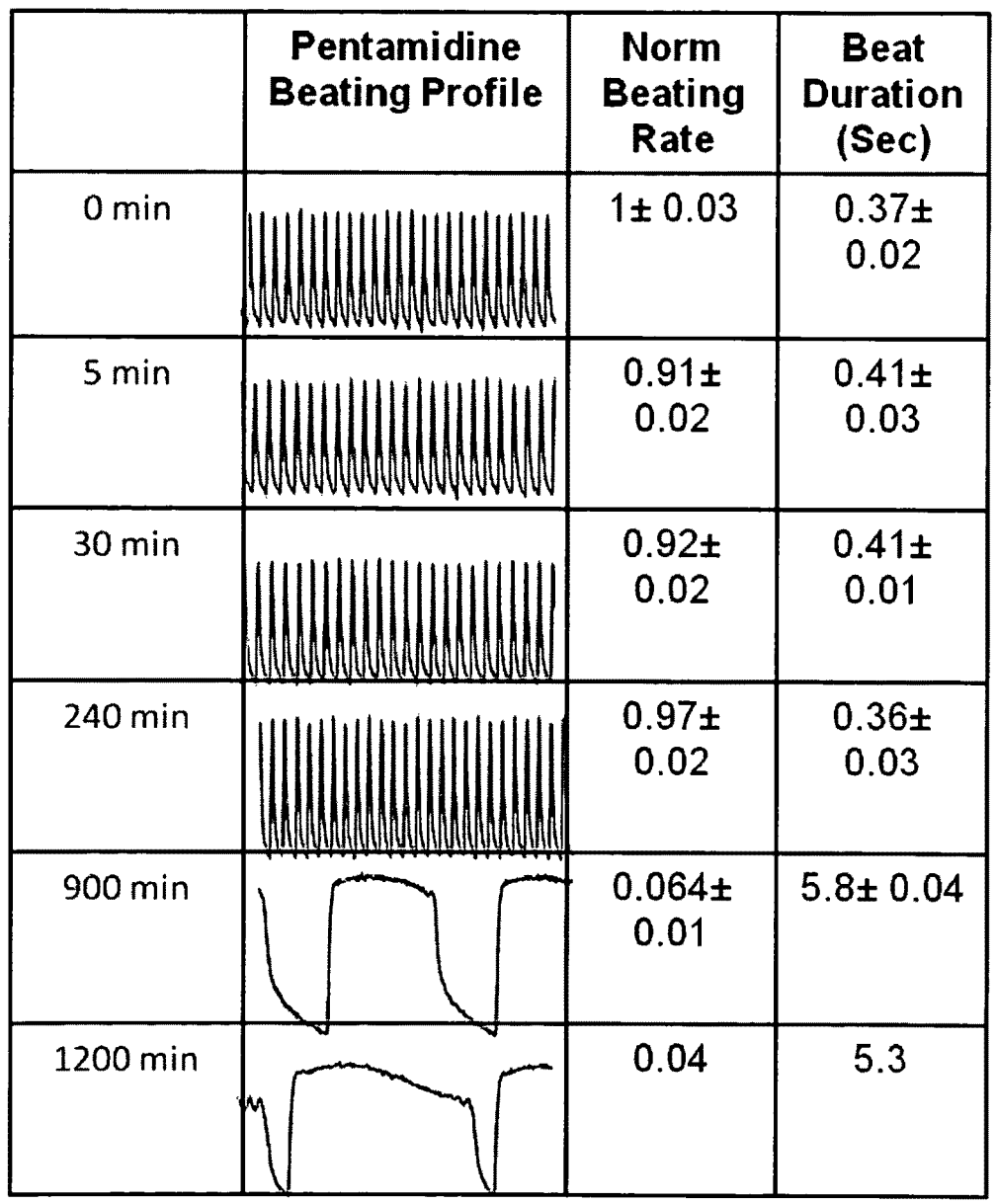

While the cardiotoxic side effect of most drugs is primarily viewed as a function of the concentration of the drug and its possible adverse interaction with other compounds, it must be emphasized that the time-dependent response of cardiomyocyte to a given concentration exposure is also an important parameter. This point is especially relevant for cardiac function where time-dependent heart rate variability or dynamics of periodicity could be a key determinant of proarrhythmic potential (Bass et al., 2008). Furthermore, an increasing number of drugs are found to inhibit hERG function by dual mechanisms of short-term channel block and long term hERG trafficking defects that operate over different time and concentration scales (van der Heyden et al., 2008). The non-invasive nature of the impedance readout allows for monitoring of cardiomyocyte response from millisecond time frame to minutes, hours and days in real-time and therefore well suited to capture time series data for these complex responses. The utility of this feature was demonstrated with respect to treatment of mouse embryoninc stem cell derived cardiomyocytes (mESCC) with both pentmidine and doxorubicin (FIGS. 14A-C). Pentmidine, a hERG trafficking inhibitor associated with TdP in the clinic had a major impact on beating rate and beat duration that was elicited about 900 min after initial exposure (Kuryshev et al., 2005). Standard manual patch clamp techniques or planar patch clamp techniques, while the golden standard, and most likely would have missed this effect because action potential recordings are typically performed within the first hour after compound exposure. Doxorubicin, an anthracycline affected both the beating rate and periodicity of beating while causing progressive and dose-dependent decrease in overall impedance signal of the cells (within 24 hours after compound exposure) most likely due to loss of viability (FIGS. 14A and B). Therefore, the ability to simultaneously capture the dynamicity of beating rate changes coupled with overall changes in impedance to reflect the global compound effect on cell health within the same assay can provide additional information regarding mechanism of toxicity.

EXAMPLES

Example 1

Detection of Changes in Cardiomyoctye Beating in Response to Administration of Pharmacologically Active Agents Cell culture. Mouse ES cell-derived cardiomyocytes (Cor.At) were obtained from Axiogenesis (Cologne, Germany, catalogue number XCAC-1010E, Lonza Cologne). The cells were kept in liquid nitrogen until thawed and cultured according to protocol provided by Axiogenesis with slight modifications. Briefly, each well of the E-PLATE (ACEA Biosciences Inc., San Diego, Calif.) was coated with 50 µl of a 1:100 diluted fibronectin (FN) solution (F1114, Sigma-Aldrich, USA) and incubated at 4° C. over night. Subsequent to removal of FN, the wells were washed with PBS and followed by cell seeding. The cells were thawed at 37° C. in a waterbath, transferred to 15 mL conical tube containing 9 ml fresh Cor.At complete culture medium (XCAM-250E, Lonza Cologne, Germany), centrifuged at 100 g for 5 minutes and the medium was replaced with small volume of fresh Cor.At complete culture medium containing puromyocin at final concentration of 10 µg/ml. The cells were counted and the percentage of viable cells determined by trypan blue exclusion method.

Monitoring of cardiomyoctye attachment and contraction. About 40000-60000 viable cells were seeded per well of a 96 well E-PLATE (ACEA Biosciences Inc., San Diego, Calif.) and the cells were monitored using the xCELLigence RTCA Cardio system (Roche Applied Science and ACEA Biosciences). Cell culture medium was replaced once on a daily basis. Typically, drug treatment was initiated 60-80 hours after cell seeding depending on seeding density. Data collection is controlled by software program which operates the hardware and allows the user to define the sampling frequency and sampling window. Sampling frequency is defined as the number of times during an experimental run the beating is sampled and the sampling window is defined as the duration of time that the beating is actually measured. For example if the sampling frequency is 15 minutes and sampling window is for 5 second means that each 15 minute the system will record beating data for 5 seconds. In a typical experiment, prior to compound treatment the sampling frequency is once every hour and the sampling window is 20 seconds. 5 min prior to treatment, the cells are sampled every minute for 20 seconds to establish baseline recording. After treatment, the sampling frequency is every minute for the first hour, every 5 minutes for the second hour and every 15 minutes for 3-24 hours. The sampling window for each recording is fixed at 20 seconds. After the data acquisition, the RTCA Cardio software is used to calculate the parameters such as beating rate, amplitude, beating period, normalized beating rate, normalized amplitude, and beating rate irregularity (BRI) index and perform subsequent basic statistics, like average and standard deviation and further supply EC50 values for dose-response testing.

Terms and Analysis Parameters. Each measured beating cycle corresponds to the excitation-contraction coupling of the cardiomyocytes. The typical measured beating pattern is illustrated in FIG. 7 and FIG. 8. The beatings are composed of a sequence of positive peaks (+P) and negative peaks (−P). The Cell Index difference between one negative peak to the following positive peak is defined as amplitude. The time between each positive peak is defined as beating period and the beating rate is calculated based on each beating period to derive how many beatings occurred in one minute. Three time-related parameters, rise time $T_r$, falling time ($T_f$, or termed as decay time $T_d$), and half-amplitude width $T_{IBD50}$, resolve the temporal beating characteristic.

For data analysis, the related parameters are calculated for every beating within one recording period and the average and standard deviation are derived correspondingly. In order to compare the effect of tested compounds, beating rate or amplitude after compound treatment are normalized to the same time point before compound treatment to obtain the normalized beating rate or normalized amplitude. In order to evaluate the degree of arrhythmia, the beating rhythm irregularity (BRI) index is derived based on the coefficient of variation (i.e. standard deviation divided by average) of the beating period during one record period.

Multi-Electrode Array. For the culture of the mouse ES cell-derived cardiomyocytes a sterilized substrate-integrated planar standard MEA (59 TiN electrodes and a grounded reference electrode, 8×8 electrode grid, electrode spacing 200, electrode diameter 30, glass ring (Multi Channel Systems GmbH, Reutlichen, Germany), 10 µl of the 1:100 diluted fibronectin solution (F1141, Sigma-Aldrich) was placed exactly on the microelectrode area of the MEA and incubated for at least 3 hours at 37° C. in an humidified incubator. Afterwards residual coating solution of taken off and 20 µl with 2×10$^4$ cardiomyocytes were placed on the coated electrode area and the complete MEA was incubated for another 3 hours at 37° C. in the incubator to establish cell adhesion before 1 ml of Cor.At culture medium was applied. The MEA was connected to the amplifier and data-acquisition system (Multi Channel Systems) with band pass filter characteristics of 0.5 Hz to 1 kHz. Spontaneous electrical activity was recorded with software (MC Rack; Multi Channel Systems) (Stett 2003). Data were recorded simultaneously from 59 channels with a sampling frequency of 10 kHz.

Cardiomyocytes on MBAs were kept in an incubator at 37° C. during the whole time period of the assay. The cells were equilibrated to the assay buffer (IMDM+0.1% FCS) for at least 45 min prior to baseline recording and subsequent substance application. After that, three increasing concentrations of the test compound were applied consecutively for 15 min each. Additional wash-out period with was at least 45 min. Analyzed parameters from extracellular recordings did not alter in a time dependent manner in time-matched control experiments of the vehicle (water or 0.1% DMSO) during all experimental phases.

Raw data from electrode array recordings was analyzed offline. Frequency was determined as the reciprocal value of the inter spike intervals of the field action potentials and field action potential duration was calculated according to Halbach et al. (2003) (Halbach et al., 2003). Frequency correction of the field potential duration was assessed according to Mitchell et al. (Mitchell et al., 1998).

Data are presented as mean values±standard error of the mean in percent of baseline. In order to evaluate compound-induced effects relative to control measurements, differences between the control group and the compound measurements were tested for statistical significance by means of unpaired Student's t-test.

Figures 9A, 9B:
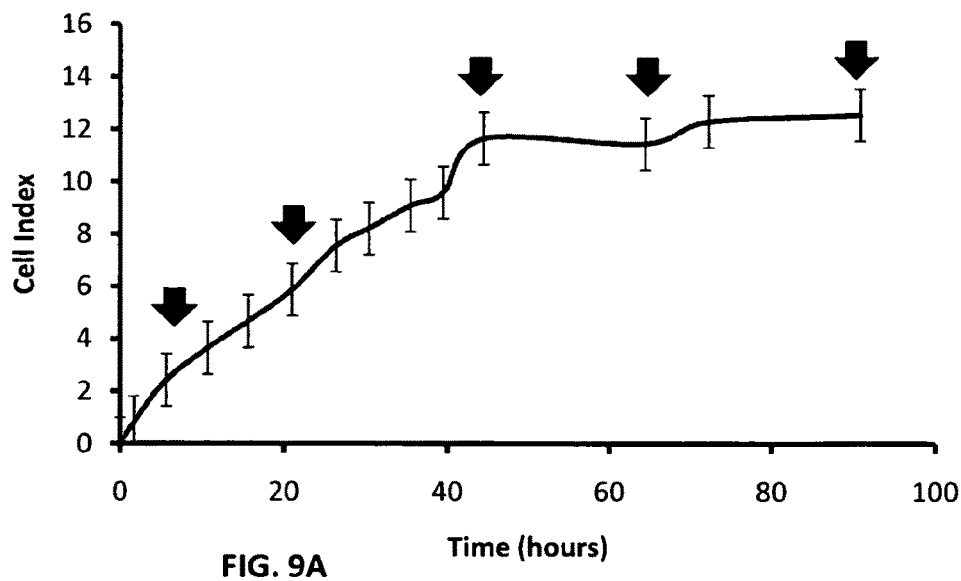
FIGS. 9A-D depicts graphs and an accompanying table resulting from dynamic monitoring and characterization of mouse embryonic stem cell derived cardiomyocytes (mESCC) beating using impedance-based detection.

Microelectronic monitoring of cardiomyocyte beating. To characterize the beating, mESCC were seeded in the wells of the E-Plate at a density of 40,000 cells/well. The cells were monitored up to 96 hours in culture (FIG. 9A) and the beating activity was recorded at 12, 24, 48, 72 and 96 hours (FIG. 9A, arrows) for a total duration of 20 seconds (FIG. 9B). Interestingly, within 24 hours after seeding the cells no consistent beating activity could be detected even though, under the microscope clusters of asynchronously beating cardiomyocytes, which have not had an opportunity to form a syncytium could be detected (data not shown). However, within 48 hours the individual clusters begin to form clear connections and the entire monolayer of cardiac cells in the bottom of the well begin to beat in a synchronous manner. Likewise, based on impedance recording, reproducible beating activity is detected by 48 hours (FIG. 9B). The beating rate at 48 hours is approximately 80 beats/minute and progressively increases with time reaching almost 250 beats/minute after a month in culture. These observations are consistent with electrophysiological monitoring of action potential duration in mouse ES cell-derived cardiomyocytes (Fijnvandraat et al., 2003).

In order to analyze the curves and quantify beating activity, 3 different analysis parameters were derived; $T_{IBD50}$, $T_r$, and $T_d$. $T_{IBD50}$ is a parameter which measures the duration (ms) between the rise and fall of beat cycle at 50% of maximal amplitude. $T_{IBD50}$ values for mESCC at corresponding times are shown in FIG. 9B. At 48 hours the $T_{IBD50}$ value is 142±4.6 ms which decreases to 105±2.4 ms by 96 hours. The initial rise in amplitude denoted as $T_r$ is relatively fast and depending on the time of recording can vary from 29±5.1 ms to 38±1.4 ms (FIG. 9B). The decay time (or the falling time as shown in FIG. 8), denoted as $T_d$, which reflects the time the signal decays from 80% of peak height to 20% of peak height is longer compared to $T_r$ and can range from 88±7.2 ms to 124±12.0 ms, depending on the time of recording (FIG. 9B). Interestingly, the kinetics of rise and fall of impedance mirrors that of calcium in mouse embryonic cardiomyocytes (Rapila et al., 2008) and it is possible that $T_r$ and $T_d$ may reflect the time for two alternating phases of the beating cycle, namely contraction and relaxation.

Figure 9C:
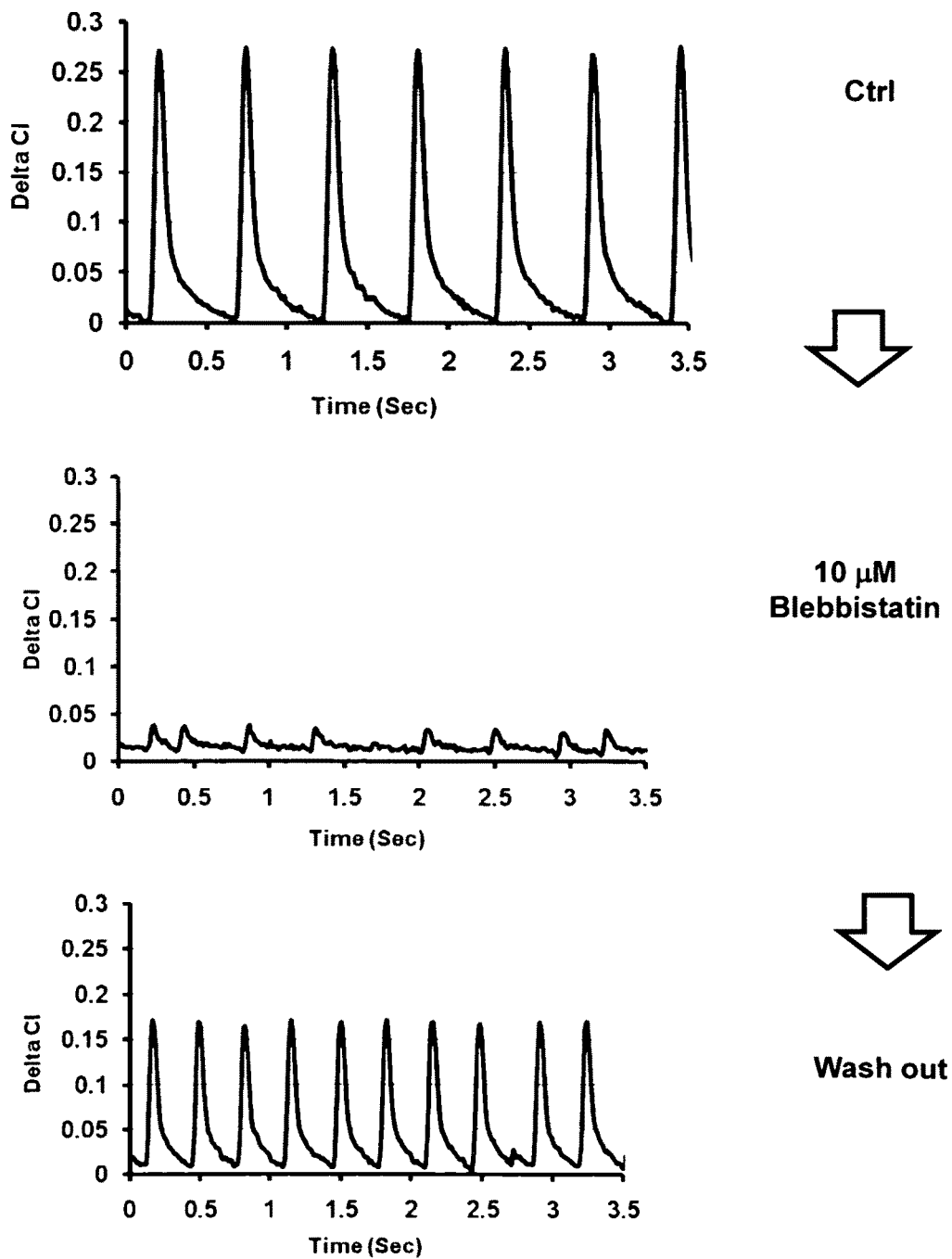
Figure 9D:
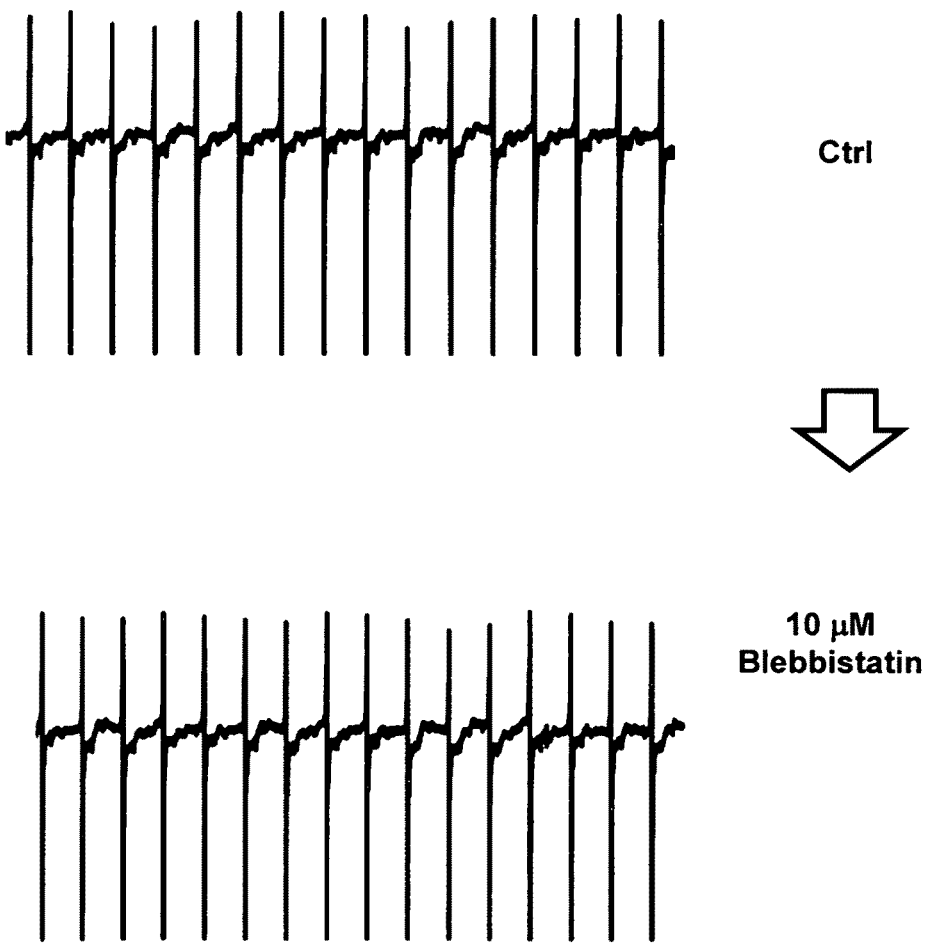

To determine if the impedance signal is reflective of physical contraction and relaxation cycle of mESCC, we used an inhibitor of the myosin heavy chain ATPase activity, blebbistatin, shown to inhibit cardiomyocyte contraction (Kovacs et al., 2004). As shown in FIG. 9C, blebbistatin treatment of mESCC resulted in significant inhibition of impedance signal, which was restored after washing the wells and culturing the cells in media without blebbistatin. Interestingly, at concentration which blebbistatin inhibited impedance measurement of beating activity, no effect on action potential duration was detected using field potential recording (FIG. 9D). The inability of electrophysiological readout to detect blebbistatin effect has also been confirmed using isolated rat and mouse ventricular myocytes, isolated rabbit ventricle, and Langendorff-perfused rabbit hearts (Dou et al., 2007; Fedorov et al., 2007) indicating that electrophysiological readouts may miss the potential side effect of compounds depending on whether the compounds affect the electrical or mechanical aspects of cardiomyocyte contraction. Overall, the results presented thus far demonstrate that impedance readout can be used to monitor the rhythmic contraction/relaxation cycle of mESCC in culture over a prolonged duration and in combination with electrophysiological readouts may be able to detect compounds that decouple excitation and contraction.

Pharmacological assessment of mESCC using impedance monitoring. Using specific pharmacological modulators of ion channel and non-ion channel targets, we set out to dissect specific events of the excitation/contraction cycle in mESCC. First, the time and dose-dependent effect of various ion channel modulators of calcium, sodium and potassium channels were tested (FIGS. 10A-C and FIGS. 11A-C). For these experiments mESCC were thawed, seeded in the wells of the E-Plate, cultured for 3 days, treated with increasing concentrations of the compounds and monitored for 24 hours using the RTCA Cardio system.

Figure 10A:
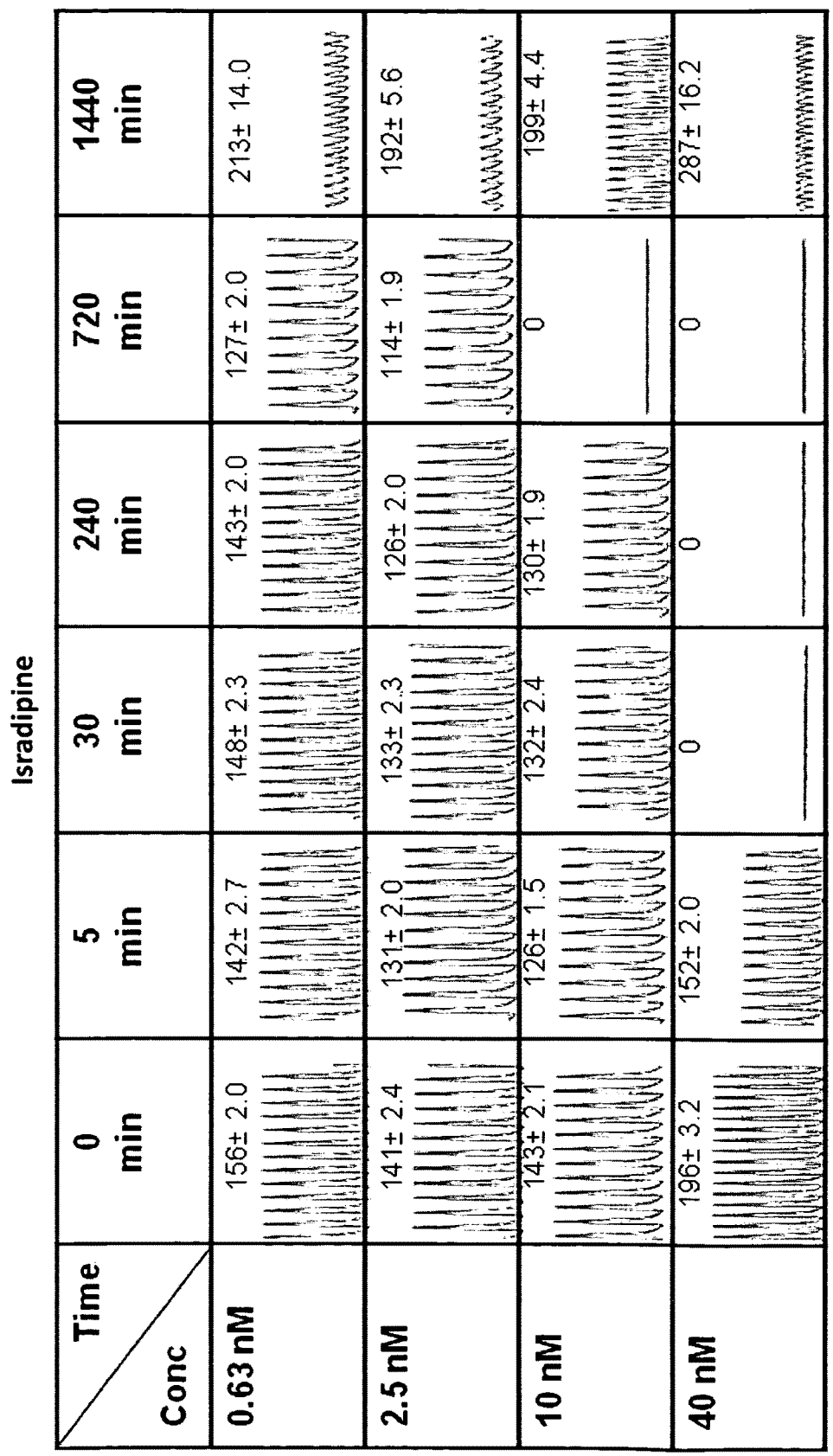
FIGS. 10A-C depict graphs showing pharmacological assessment of ion channel modulators measured using the impedance-based system on mouse embryonic stem cell derived cardiomyocytes (mESCC). Cells were seeded in the wells of the E-PLATE (ACEA Biosciences Inc., San Diego, Calif.), monitored for 3 days using the RTCA Cardio system and treated with the indicated concentrations of each compound. The beating activity was recorded by the RTCA Cardio system as described in the Examples section. For each compound at the indicated time points 5 sec of beating activity is displayed with the exception of ERG which is total of 14 seconds of beating activity. The beating rate for each interval of beating activity is displayed as beats/min−/+ SD; the data shown is one representative recording from a total of at least 3 separate experiments.
Figure 10B:
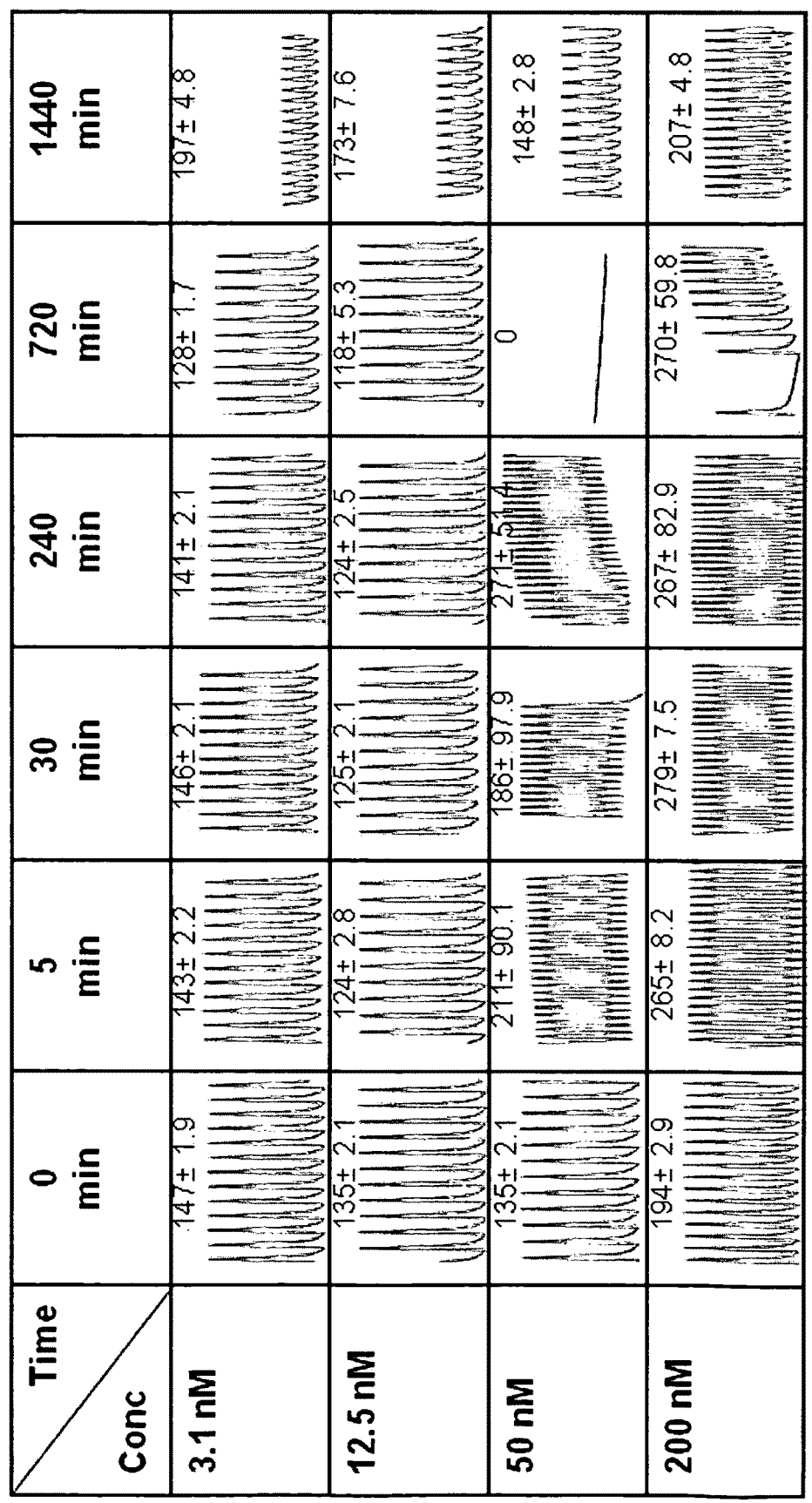

Assessment of voltage-gated calcium channels. Embryonic stem cell-derived cardiomyocytes are known to undergo spontaneous contractions due to intracellular calcium oscillations mainly initiated from the sarcoplasmic reticulum (SR) (Sachinidis et al., 2003). It is also believed that during SR-driven spontaneous activity, the plasmalemmal voltage activated calcium influx could provide a compensatory mechanism for restoring depleted calcium pools in the SR (Rapila et al., 2008). Application of isradipine, a well known voltage activated L-type calcium channel blocker of the dihydropyridine class (Triggle, 2003) caused a progressive time and dose-dependent decrease and inhibition of beating activity, indicating that calcium entry through L-type calcium channels is required for beating (FIG. 10A). The half maximal dose-response value for isradipine induced inhibition of beating activity based on measurement of normalized beating rate and amplitude is 19.7 nM and 42.3 nM respectively (at 5 min time point after compound addition; FIG. 12). These values are consistent with efficacy of isradipine tested in isolated rabbit heart (Mellemkjaer et al., 1992) as well as recombinant HEK-293 cells stably expressing the human Cav1.2 (Balasubramanian et al., 2009) (FIG. 15). The compound (S)-(–)Bay K 8644 is also of the dihydropyridine class, but acts in an agonistic mode to activate voltage-gated calcium channels (Franckowiak et al., 1985; Schramm et al., 1985). Treatment of mESCC with (S)-(–)Bay K 8644 resulted in a dose and time dependent effect that substantially increased the beating rate which persisted for up to 12 hours at higher concentration and declined by 24 hours (FIG. 10B). The increase in beating rate is consistent with the reported ionotropic action of this compound and the EC50s obtained (77 nM) for beating rate is consistent with previously published reports using rat ventricular myocytes (Zahradnikova et al. 2007) (33 nM; data not shown).

Figure 10C:
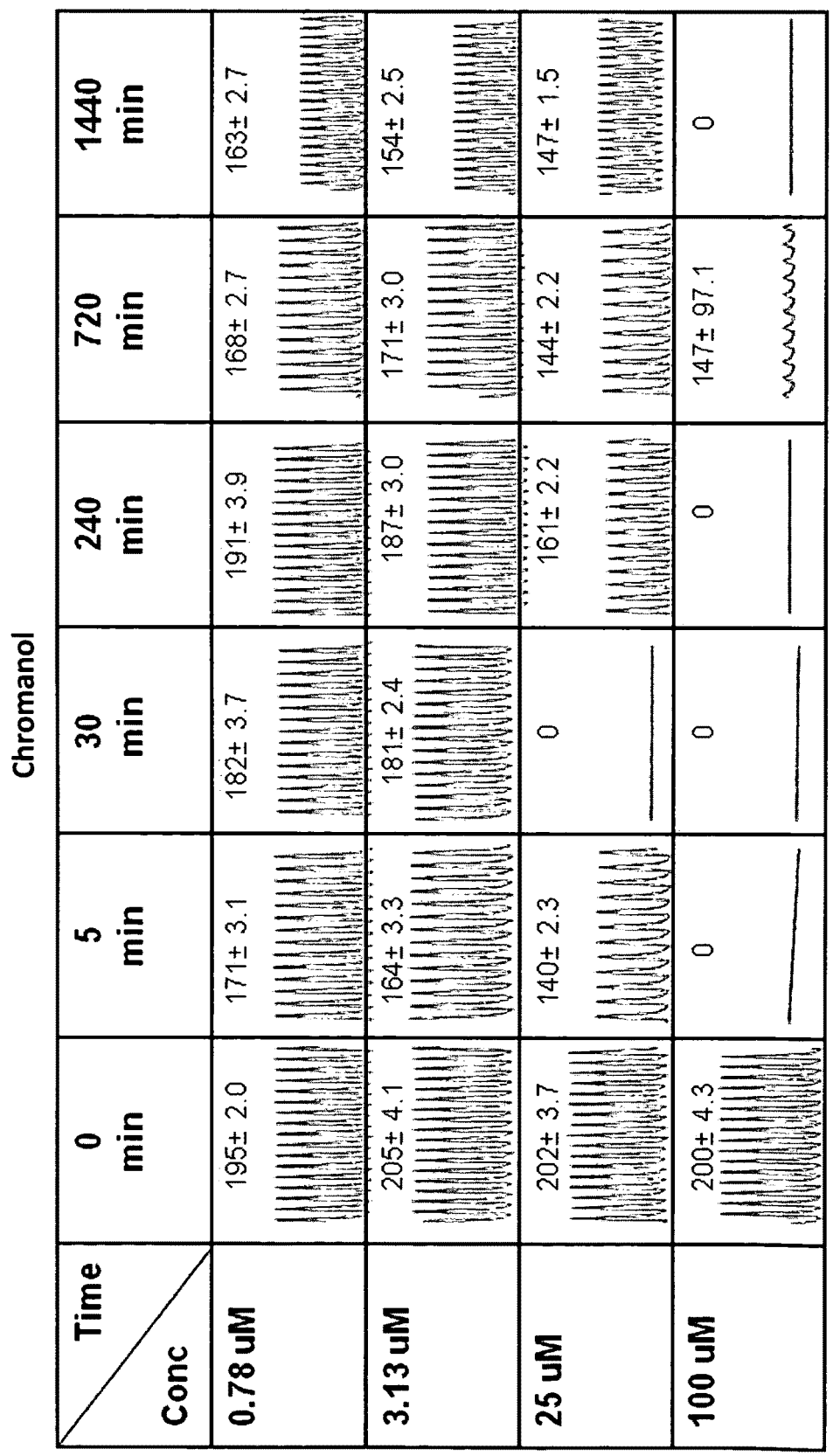

Assessment of potassium channel modulators. Next, the effect of Chromanol 293B, an inhibitor of slow activating delayed rectifier $K^+$ current ($I_{ks}$) (Bosch et al., 1998; Fujisawa et al., 2000; Ono et al., 2000) was tested (FIG. 10C). While at the highest dose (100 µM) Chromanol 293B treatment resulted in complete inhibition of cardiomyocyte beating activity, at intermediate doses it slows down the beating rate (69% and 80% of control at 25 µM and 3.13 µM, respectively 5 min post compound addition) and also prolongs the beat duration (13.0 ms and 21.1 ms at 25 µM and 3 µM respectively and at 5 min post compound addition). The $I_{ks}$ is mainly involved in the repolarization phase of the action potential and its inhibition by Chromanol 293B leads to increased action potential duration (APD) of canine ventricle myocytes (Volders et al., 2003) and stem cell-derived human cardiomyocytes (Peng et al.) as measured by electrophysiological techniques. The increased APD has been shown to slow down the decline of calcium concentrations and thereby may prolong the contraction phase of cardiomyocytes (Bouchard et al., 1995).

Figure 11A:
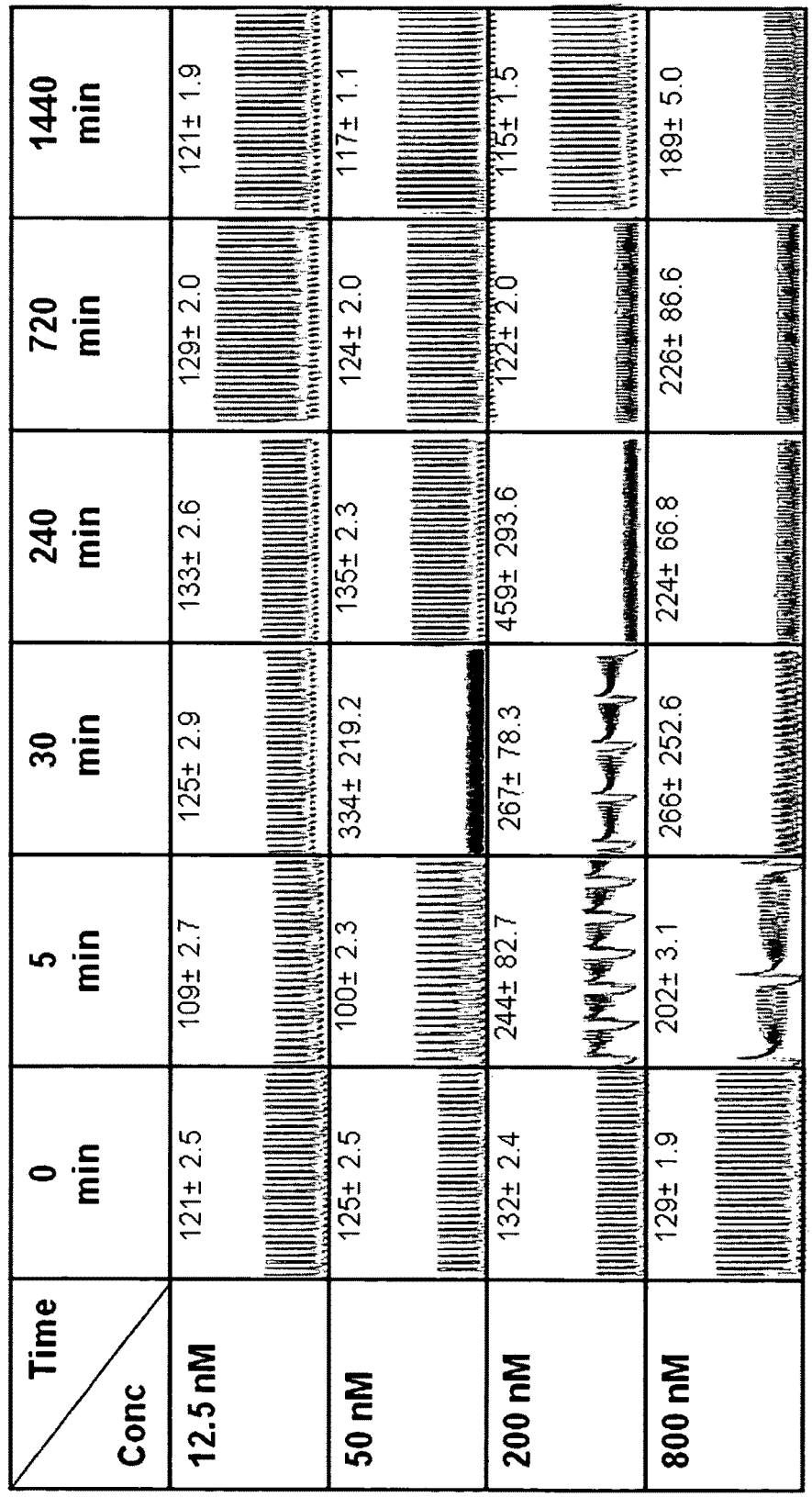
FIGS. 11A-C depict graphs showing pharmacological assessment of ERG channels, sodium channels and ionotropic agents.

The rapid activating component of the delayed rectifier current ($I_{Kr}$) is also involved in the repolarization phase of cardiac action potential and is mainly mediated through the ERG channel (Brown, 2005). The effect of E4031, a potent ERG channel inhibitor, was also tested using mESSC in a time and dose-dependent manner (FIG. 11A). As shown, E4031 treatment interrupted that normal rhythmicity of beating, especially at high concentrations (200 nM-800 nM) and resulted in prolonged beat durations which are accompanied by plateau oscillations. This phenomenon was typical of other ERG blockers as well (see next section). At the doses tested the cells appear to recover from the effect of E4031 by 24 hours after treatment. Based on normalized beating rate and beat rate irregularity parameter, the half maximal value obtained is 27 nM and 57 nM, respectively and is consistent with the reported $IC_{50}$ for E4031 (10 nM) using stem cell-derived human cardiomyocytes with patch clamp technique (Peng et al.).

Figure 11B:
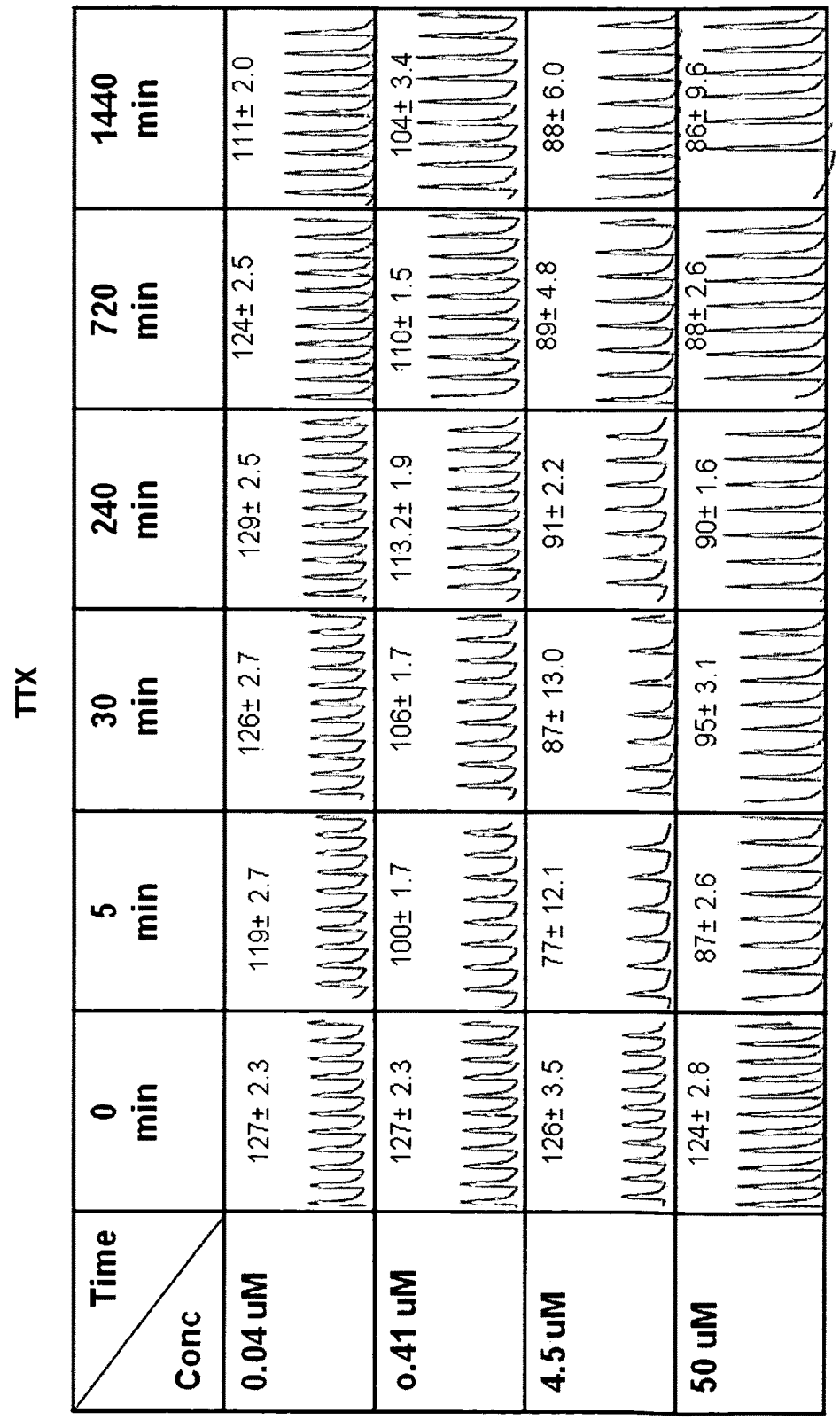

Assessment of sodium channel modulators. Voltage-gated $Na^+$ channels are primarily responsible for the $Na^+$ current and the depolarization phase of cardiac action potential. Based on gene expression and electrophysiological data, the Scn5a gene product, which encodes for the α-subunit of voltage-gated $Na^+$ channel, is present and functional within mESCC. Treatment of mESCC with Tetrodotoxin (TTX), a potent and selective inhibitor of voltage-gated $Na^+$ channels (Narahashi, 2008), led to a dose-dependent decrease in beating rate of mESCC which is sustained at the higher concentrations for the entire duration of 24 hours (FIG. 11B). The apparent half-maximal dose-response value obtained for inhibition of mESCC beating is about 0.28 µM (FIG. 12).

Figure 11C:
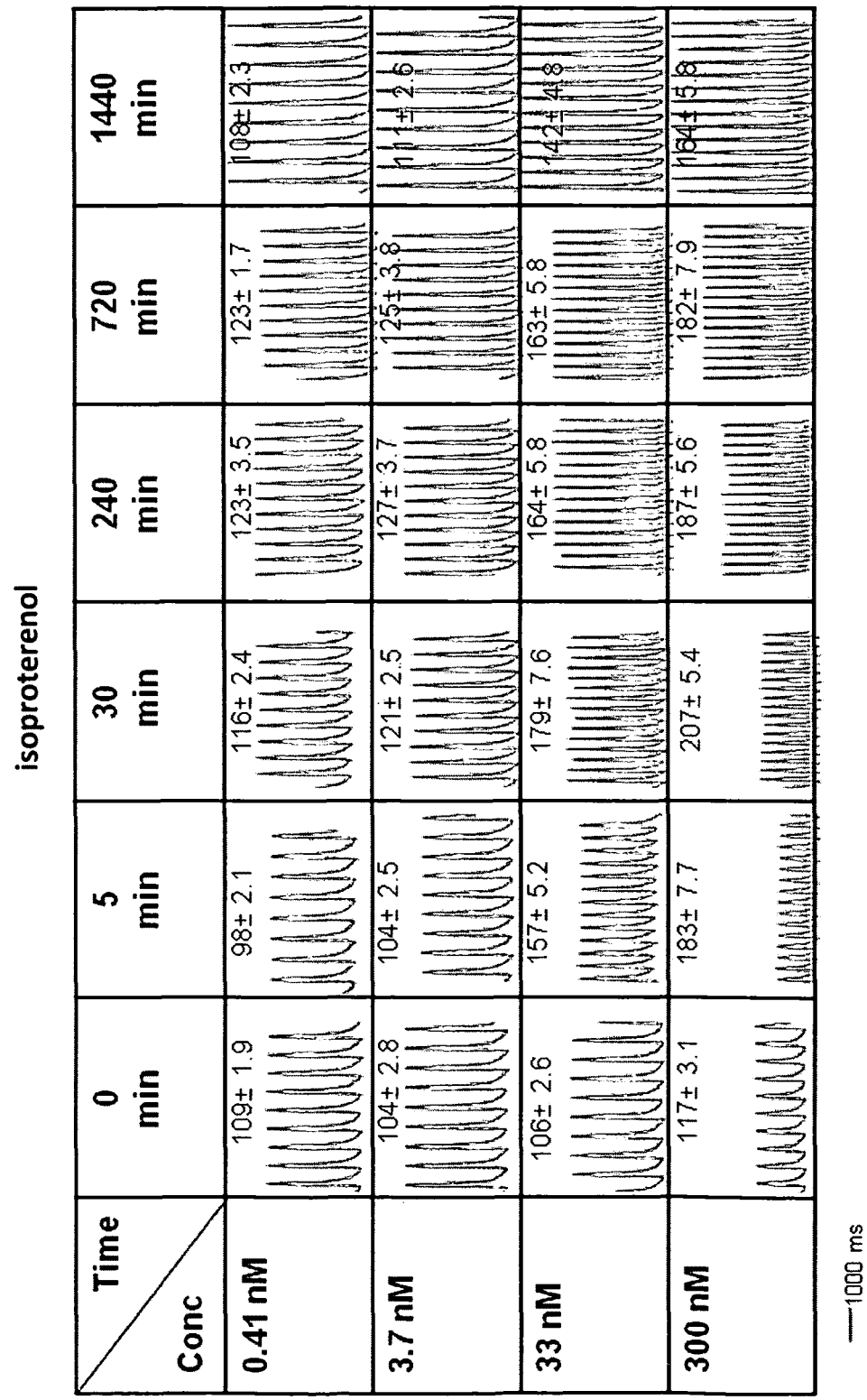

Assessment of chronotropic agents. Activation of the sympathetic nervous system and neuro-hormonal regulation through the β-adrenergic receptor is a major mechanism controlling rate and contractility of the cardiac tissue (Bers, 2002). The protein machinery responding to β-adrenergic receptor stimulation is present and functional within mESCC and its agonists are well characterized chronotropic and ionotropic stimulants (Maltsev et al., 1999). Therefore we sought to test whether β-adrenergic receptor stimulation could be detected by the RTCA Cardio system. Treatment of mESCC with Isoproterenol, a β-adrenergic receptor agonist, increased the contraction frequency of mESCC in a dose and time-dependent manner while decreasing the overall duration of each beat (FIG. 11C). The overall effect is similar to the L-type calcium channel agonist (S)-(–)Bay K 8644 (FIG. 10B) and is consistent with the observation that stimulation of β-adrenergic receptors leads to activation of L-Type calcium channels (Maltsev et al., 1999). The data presented in this section demonstrates that impedance is a sensitive readout to assess cardioymocyte beating and its modulation by pharmacologically active compounds which alter cardiac electrophysiological and/or contractile properties. Compound treatment produces both time and concentration-dependent responses which are captured in real-time by the RTCA Cardio system. Both acute and long term assessment of beating activity may provide additional mechanistic insight as demonstrated for ERG channel inhibitors in the next section.

Example 2

Mechanism-Dependent Compound Toxicity Screening: Identification of Impedance-Based Pro-Arrhythmic Signatures To test the utility of RTCA Cardio system for pre-clinical cardio-safety screening two complementary approaches were undertaken. First, 4 drugs withdrawn from the market due to increased incidence of TdP (Fermini et al., 2003) were screened in a dose-response manner using mESCC (FIG. 13A). These compounds have subsequently been shown to also inhibit hERG channel activity (Brown, 2005). All four compounds significantly affected beating rate in a dose-dependent manner (FIG. 13A) and produced beating irregularities that were consistent with those observed for E4031 in terms of beating waveform, suggesting a common underlying mechanism (FIG. 13B). We speculate that the plateau oscillation phenomenon observed by hERG channel blockers maybe related to early after depolarization (EAD) effect caused by blocking of the hERG current leading to premature activation of voltage-dependent L-Type calcium channels, calcium entry and culminating in premature contractions (Rubart et al., 2005). These signature beating waveforms were also observed for other drugs that are known to interact with and block ERG activity (FIG. 15 and see below). In order to better quantify the beating irregularities we derived a kinetic parameter referred to as beating rhythm irregularity (BRI) index which represents the coefficient of variation (standard deviation divided by average) of beating rate periods. Based on this parameter we derived half maximal concentrations for E4031 (FIG. 12), astemizole, cisapride, droperide and sertindole (FIG. 13A) which are 57 nM, 290 nM, 2700 nM, 2100 nM and 290 nM, respectively. The respective values obtained here are within the range reported for these compounds using electrophysiological methods (data not shown). These findings suggest that impedance-based beating profiles could be used in a predictive manner to screen for and identify compounds that may have off-target interactions with ERG channel.

Next, a compound library containing 50 proarrhythmic and antiarrhythmic compounds was also screened at 3 doses (10 µM, 1 µM and 0.1 µM) (FIG. 15). As shown, all known hERG blockers with the exception of Terfenadine displayed beating profiles consistent with those shown in FIG. 13B. A more extensive dose-response profiling of Terfenadine may be required in order to observe the signature beating profile similar to other hERG channel inhibitors. In addition, in this screen, compounds modulating other ion channel targets such as calcium and sodium also profoundly and dose-dependently affected beating activity.

Example 3

Assessment of Short and Long Term Cardiac Liability Using Impedance-Based Systems The true test of any in vitro assay utilized in preclinical safety assessment depends on its ability to model and predict in vivo effect in the clinic. Thus far we have shown compounds modulating ion channel activities in cardiomyocytes can be detected by the RTCA Cardio system. However, there are a number of drugs whose cardiac liability in the clinic extends beyond its propensity to just cause arrhythmia; for example the chemotherapeutic agent, doxorubicin, has been shown to induce arrhythmia (Singal et al., 1998) as well as cardiotoxicity by interfering with mitochondrial function (Minotti et al., 2004). Therefore, we wanted to determine if the RTCA Cardio system in combination with mESCC can model and predict the complex effects of doxorubicin. As shown in FIG. 14A, treatment of mESCC with doxorubicin results in time and dose-dependent decrease in global impedance readout, presumably due to loss of cardiomyocyte viability. Likewise, FIG. 14B, shows the dose- and time-dependent effect of doxorubicin on cardiomyocyte beating within the same assay. Doxorubicin treatment of mESCC leads to significant decrease in overall beating rate and also induces irregular beating pattern that has features of compounds that induce arrhythmia. While it may be difficult to draw direct parallels between in vitro assays and clinical observations, both acute and chronic effect of doxorubicin resulting in arrhythmia has been documented in the clinic (Minotti et al., 2004).

The mode of interaction of drugs with various targets within cardiomyocytes may be direct as shown for the various ERG channel blockers and those of sodium and calcium channels or it could also be indirect affecting such processes as the folding or transport of ion channel proteins to the membrane surface of cardiomyocytes (Dennis et al., 2007) and therefore may go undetected in most conventional safety studies which are geared towards identification of direct ERG blockers. This point is best exemplified by the compound pentamidine, which in the U.S. is used as a second line of treatment of Pneumocystis carinii pneumonia, a common opportunistic infection in patients with impaired immune function. Pentamidine has been shown to affect the transport of the ERG channel to the membrane in heterologuous expression systems as well as in cardiac myocytes with repolarization being delayed as a direct consequence (Dennis et al., 2007; Kuryshev et al., 2005). Since this compound affects ERG channel activity indirectly, its effect will be manifested in a time-dependent manner and difficult to capture by standard patch clamp techniques which are limited to the first hour of recording time. We tested the effect of pentamidine on mESCC in a time dependent manner (FIG. 14C). Administration of pentamidine at a final concentration of 20 µM has no noticeable effect on beating rate and amplitude well into 900 min after compound addition, at which point the beating rate slows down and the beating duration is significantly delayed, most likely due to extended repolarization phase. These observations highlight the importance of monitoring compound effect in a time-dependent manner in order to resolve the effect of compounds on both early and longer term function of cardiomyocytes and to obtain greater mechanistic understanding.

REFERENCES

Abassi Y A, Xi B, Zhang W, Ye P, Kirstein S L, Gaylord M R, et al. (2009). Kinetic cell-based morphological screening: prediction of mechanism of compound action and off-target effects. *Chem Biol* 16(7): 712-723.

Atienza J M, Yu N, Kirstein S L, Xi B, Wang X, Xu X, et al. (2006a). Dynamic and label-free cell-based assays using the real-time cell electronic sensing system. *Assay Drug Dev Technol* 4(5): 597-607.

Atienza J M, Yu N, Wang X, Xu X, Abassi Y (2006b). Label-free and real-time cell-based kinase assay for screening selective and potent receptor tyrosine kinase inhibitors using microelectronic sensor array. *J Biomol Screen* 11(6): 634-643.

Balasubramanian B, Imredy J P, Kim D, Penniman J, Lagrutta A, Salata J J (2009). Optimization of Ca(v)1.2 screening with an automated planar patch clamp platform. *J Pharmacol Toxicol Methods* 59(2): 62-72.

Bass A S, Darpo B, Breidenbach A, Bruse K, Feldman H S, Games D, et al. (2008). International Life Sciences Institute (Health and Environmental Sciences Institute, HESI) initiative on moving towards better predictors of drug-induced torsades de pointes. *Br J Pharmacol* 154(7): 1491-1501.

Bers D M (2002). Cardiac excitation-contraction coupling. *Nature* 415(6868): 198-205.

Bosch R F, Gaspo R, Busch A E, Lang H J, Li G R, Nattel S (1998). Effects of the chromanol 293B, a selective blocker of the slow, component of the delayed rectifier K+ current, on repolarization in human and guinea pig ventricular myocytes. *Cardiovasc Res* 38(2): 441-450.

Bouchard R A, Clark R B, Giles W R (1995). Effects of action potential duration on excitation-contraction coupling in rat ventricular myocytes. Action potential voltage-clamp measurements. *Circ Res* 76(5): 790-801, Brown A M (2005). HERG block, QT liability and sudden cardiac death. *Novartis Found Symp* 266: 118-131; discussion 131-115, 155-118.

Denning C, Anderson D (2008). Cardiomyocytes from human embryonic stem cells as predictors of cardiotoxicity. *Drug Discovery Today* 5(4): 223-232.

Dennis A, Wang L, Wan X, Ficker E (2007). hERG channel trafficking: novel targets in drug-induced long QT syndrome. *Biochem Soc Trans* 35(Pt 5): 1060-1063.

Doetschman T C, Eistetter H, Katz M, Schmidt W, Kemler R (1985). The in vitro development of blastocyst-derived embryonic stem cell lines: formation of visceral yolk sac, blood islands and myocardium. *J Embryol Exp Morphol* 87: 27-45.

Dou Y, Arlock P, Arner A (2007). Blebbistatin specifically inhibits actin-myosin interaction in mouse cardiac muscle. *Am J Physiol Cell Physiol* 293(3): C1148-1153.

Fedorov V V, Lozinsky I T, Sosunov E A, Anyukhovsky E P, Rosen M R, Balke C W, et al. (2007). Application of blebbistatin as an excitation-contraction uncoupler for electrophysiologic study of rat and rabbit hearts. *Heart Rhythm* 4(5): 619-626.

Fermini B, Fossa A A (2003). The impact of drug-induced QT interval prolongation on drug discovery and development. *Nat Rev Drug Discov* 2(6): 439-447.

Fijnvandraat A C, van Ginneken A C, de Boer P A, Ruijter J M, Christoffels V M, Moorman A F, et al. (2003). Cardiomyocytes derived from embryonic stem cells resemble cardiomyocytes of the embryonic heart tube. *Cardiovasc Res* 58(2): 399-409.

Franckowiak G, Bechem M, Schramm M, Thomas G (1985). The optical isomers of the 1,4-dihydropyridine BAY K 8644 show opposite effects on Ca channels. *Eur J Pharmacol* 114(2): 223-226.

Freund C, Mummery CL (2009). Prospects for pluripotent stem cell-derived cardiomyocytes in cardiac cell therapy and as disease models. *J Cell Biochem* 107(4): 592-599.

Fujisawa S, Ono K, Iijima T (2000). Time-dependent block of the slowly activating delayed rectifier K(+) current by chromanol 293B in guinea-pig ventricular cells. *Br J Pharmacol* 129(5): 1007-1013.

Halbach M, Egert U, Hescheler J, Banach K (2003). Estimation of action potential changes from field potential recordings in multicellular mouse cardiac myocyte cultures. *Cell Physiol Biochem* 13(5): 271-284.

Kamp T J, Lyons G E (2009). On the road to iPS cell cardiovascular applications. *Circ Res* 105(7): 617-619.

Kettenhofen R, Bohlen H (2008). Preclinical assessment of cardiac toxicity. *Drug Discovery Today* 13(15/16): 702-707.

Kirstein S L, Atienza J M, Xi B, Zhu J, Yu N, Wang X, et al. (2006). Live cell quality control and utility of real-time cell electronic sensing for assay development. *Assay Drug Dev Technol* 4(5): 545-553.

Kolossov E, Bostani T, Roell W, Breitbach M, Pillekamp F, Nygren J M, et al. (2006). Engraftment of engineered ES cell-derived cardiomyocytes but not BM cells restores contractile function to the infarcted myocardium. *J Exp Med* 203(10): 2315-2327.

Kolossov E, Lu Z, Drobinskaya I, Gassanov N, Duan Y, Sauer H, et al. (2005). Identification and characterization of embryonic stem cell-derived pacemaker and atrial cardiomyocytes. *FASEB J* 19(6): 577-579.

Kovacs M, Toth J, Hetenyi C, Malnasi-Csizmadia A, Sellers J R (2004). Mechanism of blebbistatin inhibition of myosin II. *J Biol Chem* 279(34): 35557-35563.

Kuryshev Y A, Ficker E, Wang L, Hawryluk P, Dennis A T, Wible B A, et al. (2005). Pentamidine-induced long QT syndrome and block of hERG trafficking. *J Pharmacol Exp Ther* 312(1): 316-323.

Lu H R, Vlaminckx E, Hermans A N, Rohrbacher J, Van Ammel K, Towart R, et al. (2008). Predicting drug-induced changes in QT interval and arrhythmias: QT-shortening drugs point to gaps in the ICHS7B Guidelines. *Br J Pharmacol* 154(7): 1427-1438.

Maltsev V A, Ji G J, Wobus A M, Fleischmann B K, Hescheler J (1999). Establishment of beta-adrenergic modulation of L-type Ca2+ current in the early stages of cardiomyocyte development. *Circ Res* 84(2): 136-145.

Mellemkjaer S, Bang L, Nielsen-Kudsk F (1992). Isradipine dynamics and pharmacokinetics in the isolated rabbit heart. *Pharmacol Toxicol* 70(5 Pt 1): 366-372.

Minotti G, Menna P, Salvatorelli E, Cairo G, Gianni L (2004). Anthracyclines: molecular advances and pharmacologic developments in antitumor activity and cardiotoxicity. *Pharmacol Rev* 56(2): 185-229.

Mitchell G F, Jeron A, Koren G (1998). Measurement of heart rate and Q-T interval in the conscious mouse. *Am J Physiol* 274(3 Pt 2): H747-751.

Narahashi T (2008). Tetrodotoxin: a brief history. *Proc Jpn Acad Ser B Phys Biol Sci* 84(5): 147-154.

Ono K, Shibata S, Iijima T (2000). Properties of the delayed rectifier potassium current in porcine sino-atrial node cells. *J Physiol* 524(Pt 1): 51-62.

Peng S, Lacerda A E, Kirsch G E, Brown A M, Bruening-Wright A The action potential and comparative pharmacology of stem cell-derived human cardiomyocytes. *J Pharmacol Toxicol Methods* 61(3): 277-286.

Pouton C W, Haynes J M (2007). Embryonic stem cells as a source of models for drug discovery. *Nat Rev Drug Discov* 6(8): 605-616.

Rapila R, Korhonen T, Tavi P (2008). Excitation-contraction coupling of the mouse embryonic cardiomyocyte. *J Gen Physiol* 132(4): 397-405.

Roden D M (2004). Drug-induced prolongation of the QT interval. *N Engl J Med* 350(10): 1013-1022.

Rubart M, Zipes D P (2005). Mechanisms of sudden cardiac death. *J Clin Invest* 115(9): 2305-2315.

Sachinidis A, Fleischmann B K, Kolossov E, Wartenberg M, Sauer H, Hescheler J (2003). Cardiac specific differentiation of mouse embryonic stem cells. *Cardiovasc Res* 58(2): 278-291.

Schramm M, Towart R, Kazda S, Thomas G, Franckowiak G (1985). Calcium agonism, a new mechanism for positive inotropy. Hemodynamic effects and mode of action of BAY K 8644. *Adv Myocardiol* 6: 59-70.

Shah R R (2005). Drugs, QT interval prolongation and ICH E14: the need to get it right. *Drug Saf* 28(2): 115-125.

Singal P K, Iliskovic N (1998). Doxorubicin-induced cardiomyopathy. *N Engl J Med* 339(13): 900-905.

Triggle D J (2003). 1,4-Dihydropyridines as calcium channel ligands and privileged structures. *Cell Mol Neurobiol* 23(3): 293-303.

Valentin J P Reducing QT liability and proarrhythmic risk in drug discovery and development. *Br J Pharmacol* 159(1): 5-11.

van der Heyden M A, Smits M E, Vos M A (2008). Drugs and trafficking of ion channels: a new pro-arrhythmic threat on the horizon? *Br J Pharmacol* 153(3): 406-409.

Volders P G, Stengl M, van Opstal J M, Gerlach U, Spatjens R L, Beekman J D, et al. (2003). Probing the contribution of IKs to canine ventricular repolarization: key role for beta-adrenergic receptor stimulation. *Circulation* 107 (21): 2753-2760.

Volders P G, Vos M A, Szabo B, Sipido K R, de Groot S H, Gorgels A P, et al. (2000). Progress in the understanding of cardiac early afterdepolarizations and torsades de pointes: time to revise current concepts. *Cardiovasc Res* 46(3): 376-392.

Xi B, Yu N, Wang X, Xu X, Abassi Y A (2008). The application of cell-based label-free technology in drug discovery. *Biotechnol J* 3(4): 484-495.

Zahradnikova A, Minarovic I, Zahradnik I (2007). Competitive and cooperative effects of Bay K8644 on the L-type calcium channel current inhibition by calcium channel antagonists. *J Pharmacol Exp Ther* 322(2): 638-645.

What is claimed is:

1. A method of determining a beating parameter for cardiomyocyte beating analysis, comprising:
    a) providing a cell analysis device comprising wells, each well comprising a sensor that measures cell-substrate impedance to monitor beating of cardiomyoctes in millisecond time resolution;
    b) adding cardiomyocytes to the wells;
    c) monitoring cell-substrate impedance of beating cardiomyocytes in millisecond time resolution to obtain a plurality of beating measurements; and
    d) calculating one or more beating parameters from the plurality of beating measurements.

2. The method according to claim 1, wherein the cell analysis device is an impedance monitoring device and wherein each sensor comprises two electrode structures, each having substantially the same surface area.

3. The method according to claim 1, wherein the step of calculating one or more beating parameters comprises plotting the plurality of beating measurements over a time course to form a beating curve and deriving the one or more beating parameters from the beating curve.

4. The method according to claim 1, wherein the one or more beating parameters are selected from the group consisting of beating rate, beating amplitude, rising time, falling time, beating period, IBD10, IBD50, IBD90, rising slope and falling slope.

5. The method according to claim 1, wherein the one or more beating parameters are selected from the group consisting of normalized beating rate, normalized beating amplitude, beating pattern similarity and beating rhythm irregularity.

6. The method according to claim 1, wherein the one or more beating parameters comprises 5 beating parameters.

7. The method according to claim 1, wherein the one or more beating parameters are calculated while the device continues to monitor the beating of the cardiomyocytes.

8. A method of determining a dose response for a test compound on a cardiomyocyte population, the method comprising:
    a) determining a beating parameter for different doses of a test compound according to the method of claim 1, wherein the test compound is added at different doses to the wells of the device; and
    b) plotting the beating parameters for each dose to form a dose response curve.

9. The method according to claim 8, wherein the beating parameter for each dose is from a same time point.

10. The method according to claim 8, further comprising determining a IC50 or EC50 value from the dose response curve.

11. A method for identifying a compound having a potentially cardiotoxic effect, comprising:
    a) providing a test compound suspected of having a cardiotoxic effect;
    b) performing the method according to claim 1 to obtain a beating parameter for the test compound, wherein the test compound is added to the wells; and
    c) comparing the beating parameter for the test compound to a control beating parameter to identify whether there is a difference between beating parameters and if so, concluding the test compound has the potentially cardiotoxic effect.

12. The method according to claim 11, wherein the beating parameter for the test compound comprises 2 beating parameters, which are compared to 2 control beating parameters, further wherein the test compound is concluded to have a cardiotoxic effect if at least one of the compared parameters is different.

13. The method according to claim 11, wherein the compound is suspected of being a pro-arrhythmic drug that may induce arrhythmia.

14. The method according to claim 1, further comprising adding a test compound to at least one well, wherein the step of monitoring the beating of the cardiomyocytes is performed after adding the test compound.

15. The method according to claim 14, wherein the step of monitoring the beating of cardiomyocytes is also performed before adding the test compound.

16. The method according to claim 14, wherein the test compound is added at different doses to different wells.

17. The method according to claim 1, wherein the millisecond resolution is characterized as consecutive impedance measurements less than 40 milliseconds apart.

18. The method according to claim 17, wherein the millisecond resolution is characterized as consecutive impedance measurements less than 20 milliseconds apart.

* * * * *